US008173596B2

(12) United States Patent
Goy et al.

(10) Patent No.: US 8,173,596 B2
(45) Date of Patent: May 8, 2012

(54) PROUROGUANYLIN, AND SYNTHETIC ANALOGS OR PROTEOLYTIC CLEAVAGE PRODUCTS DERIVED FROM IT, AS THERAPEUTIC AND DIAGNOSTIC AGENTS FOR DISEASES INVOLVING SALT AND/OR FLUID HOMEOSTASIS

(75) Inventors: Michael F. Goy, Chapel Hill, NC (US); Nicholas G. Moss, Carrboro, NC (US); Xun Qian, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 579 days.

(21) Appl. No.: 11/596,493

(22) PCT Filed: May 16, 2005

(86) PCT No.: PCT/US2005/016937
§ 371 (c)(1),
(2), (4) Date: Jul. 17, 2007

(87) PCT Pub. No.: WO2006/001931
PCT Pub. Date: Jan. 5, 2006

(65) Prior Publication Data
US 2008/0221022 A1  Sep. 11, 2008

Related U.S. Application Data

(60) Provisional application No. 60/571,172, filed on May 14, 2004.

(51) Int. Cl.
*A61K 38/00* (2006.01)
*A61P 9/00* (2006.01)
*A61P 9/12* (2006.01)
*A61P 7/10* (2006.01)

(52) U.S. Cl. .................... 514/12.4; 514/16.4; 514/15.6; 514/15.7; 514/869

(58) Field of Classification Search .................. None
See application file for complete search history.

(56) References Cited

U.S. PATENT DOCUMENTS

| 5,234,933 | A | 8/1993 | Marnett et al. |
| 5,326,902 | A | 7/1994 | Seipp et al. |
| 5,489,670 | A | 2/1996 | Currie et al. |
| 5,879,656 | A | 3/1999 | Waldman |
| 6,180,082 | B1 | 1/2001 | Woltering et al. |

FOREIGN PATENT DOCUMENTS

| WO | WO93/25521 | 12/1993 |
| WO | WO 97/06258 | 2/1997 |
| WO | WO 97/20049 | 6/1997 |

OTHER PUBLICATIONS

Hidaka et al., JBC. 2000; 275: 25155-25162.*
Forte et al., Am J Kidney Disease. 1996; 28: 296-304.*
DE19528544 (machine tranlated), was downloaded from the European Patent Office was obtained by use by the Examiner; 6 pages total.*
The website downloaded at nlm.nih.gov/medlineplus/ency/article/000147.htm; Jul. 17, 2009; 2 pages.*
Gradman et al., Curr Hypertens Rep. 2002; 4: 343-9.*
Moss et al., Am J Physiol Renal Physiol. 2010, 299: F1433-F1442.*
International Search Report and the Written Opinion of the International Searching Authority, or the Declaration corresponding to the PCT Application No. PCT/US05/16937 dated Sep. 18, 2006.
Nakazato et al. Identification of biologically active and inactive human uroguanylins in plasma and urine and their increases in rental insufficiency. *Biochemical and Biophysical Research Communications*, vol. 220, (1996), pp. 586-593.
Ohbayashi et al. Both inhalant and intravenous uroguanylin inhibit leukitriene C4-induced airway changes. *Peptides*, vol. 21, (2000), pp. 1467-1472.
Sierra-Johnson, J. Inhaled furosemide: a whole new mechanism of action. *Medical Hypotheses*, vol. 58, No. 6, (2002), pp. 529-530.
International Preliminary Report on the Patentability corresponding to the PCT Application No. PCT/US05/16937 dated Nov. 23, 2006.
Barber et al., "Prostaglandin blockade impairs denervation diuresis and natriuresis in the rat," American Physiological Society. pp. F895-F900 (1986).
Bettencourt et al., "Prognostic information provided by serial measurement of brain natriuretic peptide in heart failure," International Journal of Cardiology. vol. 93 pp. 45-48 (2004).
Burger, A.J., and Silver, M.A., "Nesiritide in acute heart failure," The Lancet. vol. 362 p. 998 (2003).
Carey, "Evidence for a splanchnic sodium input monitor regulating renal sodium excretion in man. Lack of dependence upon aldosterone," Circulation Research. vol. 43 pp. 19-23 (1978).
Carrithers et al., "Guanylyl cyclase C is a selective marker for metastatic colorectal tumors in human extraintestinal tissues," PNAS. vol. 93 pp. 14827-14832 (1996).
Carrithers et al., "Increased urinary excretion of uroguanyln in patients with congestive heart failure," Am. J. Physiol. Heart Cir. Physiol. vol. 278 pp. H538-H547 (2000).
Carrithers et al., "Renal effects of uroguanylin and guanylin in vivo," Brazilian Journal of Medicinal and Biological Research. vol. 32 pp. 1337-1344 (1999).
Carrithers et al., "Site-specific effects of dietary salt intake on guanylin and uroguanylin mRNA expression in rat intestine," Regulatory Peptides. vol. 107 pp. 87-95 (2002).
Cianflone et al., "Metabolic response of Acylation Stimulating Protein to an oral fat load," J. Lipid Res. vol. 30 pp. 1727-1733 (1989).
Cohen et al., "Immunohistochemical localization of guanylin in the rat small intestine and colon," Biochemical and Biophysical Research Communications. vol. 209, No. 3 pp. 803-808 (1995).
Colindres et al., "Functional evidence for renorenal reflexes in the rat," The American Physiological Society. pp. F265-F270 (1980).

(Continued)

*Primary Examiner* — Bridget E Bunner
*Assistant Examiner* — Christina Borgeest
(74) *Attorney, Agent, or Firm* — Jenkins, Wilson, Taylor & Hunt, P.A.

(57) ABSTRACT

A method for treating a disorder characterized by salt retention, fluid retention, and combinations thereof. A method for determining the presence of or the progression of a disorder characterized by salt retention, fluid retention, salt loss, fluid loss, and combinations thereof. An immunoassay kit for detecting a level of prouroguanylin in a sample.

8 Claims, 11 Drawing Sheets

OTHER PUBLICATIONS

Currie et al, "Guanylin: An endogenous activator of intestinal guanylate cyclase," PNAS. vol. 89 pp. 947-951 (1992).

Dharmsathaphorn et al., "A human colonic tumor cell line that maintains vectorial electrolyte transport," Rapid Communications. pp. G204-G208 (1984).

English et al., "Plasma Adioponectin Increases Postprandially in Obese, but not in Lean, Subjects," Obesity Research. vol. 11, No. 7 pp. 839-844 (2003).

Forte et al., "Guanylin peptides: renal actions mediated by cyclic GMP," Am. J. Physiol. Renal Physiol. vol. 278 pp. F180-F191 (2000).

Genbank Accession No. NP_071620 [*Rattus norvegicus*].

Giannella, R.A., and Mann, E.A., "*E. Coli* Heat-Stable Enterotoxin and Guanylyl Cyclase C: New Functions and Unsuspected Actions," Transactions of the American Clinical and Climatological Association, vol. 114 pp. 67-86 (2003).

Guarino et al., "$T_{84}$ cell receptor binding and guanyl cyclase activation by *Escherichia coil* heat-stable toxin," Am. J. Physiol. pp. G775-G780 (1987).

Haberle et al., "Is cerebral control of plasma [Na] a major determinant for systemic sodium balance?" Kidney International. vol. 54, Suppl. 67 pp. S-242-S-244 (1998).

Hague, Kathleen L., "Summary of the Most Common Diuretics," Pulmonary Hypertension: The Complete Resource. pp. 1-3.

Hamra et al., "Prouroguanylin and Proguanylin: Purification from Colon, Structure, and Modulation of Bioactivity by Proteases," Endocrinology. vol. 137, No. 1 pp. 257-265 (1996).

Hamra et al., "Uroguanylin: Structure and activity of a second endogenous peptide that stimulates intestinal guanylate cyclase," PNAS. vol. 90 pp. 10464-10468 (1993).

Huott et al., "Mechanism of Action of *Escherichia coli* Heat Stable Enterotoxin in Human Colonic Cell Line," J. Clin. Invest. vol. 82 pp. 514-523 (1988).

Inagami, "Atrial natriuretic factor as a volume regulator," The Journal of Clinical Pharmacology. vol. 34 pp. 424-426 (1994).

Ise et al., "Sodium balance and blood pressure response to salt ingestion in uninephrectomized rats," Kidney International. vol. 54, Suppl. 67 pp. S-245-S-249 (1998).

Kinoshita et al., "Plasma and Urine Levels of Uroguanylin, a New Natriuretic Peptide, in Nephrotic Syndrome," Nephron, vol. 81 pp. 160-164 (1999).

Kinoshita et al., "Urine and plasma levels of uroguanylin and its molecular forms in renal diseases," Kidney International. vol. 52 pp. 1028-1034 (1997).

Kita et al., "Characterization of humna uroguanylin: a member of the guanylin peptide family," Am. J. Physiol., vol. 266 pp. F342-F348 (1994).

Koller et al. "Selective Activation of the B Natriuretic Peptide Receptor by C-Type Natriuretic Peptide (CNP)," Science. vol. 252, No. 5002 pp. 120-123 (1991).

Kuhn, "Structure, Regulation, and Function of Mammalian Membrane Guanylyl Cyclase Receptors, With a Focus on Guanylyl Cyclase-A," Circulation Research. vol. 93 pp. 700-709 (2003).

Li et al., "Purification, cDNA sequence, and tissue distribution of rat uroguanylin," Regulatory Peptides. vol. 68 pp. 45-56 (1997).

Lorenz et al., "Uroguanylin knockout mice have increased blood pressure and impaired natriuretic response to enteral NaCl load," Journal of Clinical Investigation. vol. 112 pp. 1244-1254 (2003).

Lorenz, J.N., and Gruenstein, E., "A simple, nonradioactive method for evaluating single-nephron filtration rate using FITC-inulin," Am. J. Physiol. Renal Physiol. vol. 276 pp. 172-177 (1999).

Martin et al., "Regulated, Side-Directed Secretion of Proguanylin from Isolated Rat Colonic Mucosa," Endocrinology. vol. 140, No. 11 pp. 5022-5029 (1999).

Matheson et al., "Glucose and Glutamine Gavage Increase Portal Vein Nitric Oxide Metabolite Levels via Adenosine A2b Activation," Journal of Surgical Research. vol. 84 pp. 57-63 (1999).

Miyazato et al., "Uroguanylin gene expression in the alimentary tract and extra-gastrointestinal tissues," FEBS Letters. vol. 398 pp. 170-174 (1996).

Moro et al., "Release of Guanylin Immunoreactivity from the Isolated Vascularly Perfused Rat Colon," Endocrinology. vol. 141, No. 7 pp. 2594-2599 (2000).

Mu et al., "Lithium evokes a more pronounced natriuresis when administered orally than when given intravenously to salt-depleted rats," Eur. J. Physiol. vol. 438 pp. 159-164 (1999).

Nakazato et al., "Tissue Distribution, Cellular Source, and Structural Analysis of Rat Immunoreactive Uroguanylin," Endocrinology. vol. 139, No. 12 pp. 5247-5254 (1998).

Nilsson et al., "Bipolarity of duodenal enterochromaffin cells in the rat," Cell and Tissue Research. vol. 248 pp. 49-54 (1987).

Nishida et al., "Suppression of renal sympathetic nerve activity during portal vein infusion of hypertonic saline," Am. J. Physiol, Regulatory Integrative Comp. Physiol. vol. 274 pp. 97-103 (1998).

Oda et al., "Pharmacological Profile of HS-142-1, A Novel Nonpeptide Atrial Natriuretic Peptide (ANP) Antagonist of Microbial Origin. II. Restoration by HS-142-1 of ANP-Induced Inhibition of Aldosterone Production in Adrenal Glomerulosa Cells," The Journal of Pharmacology and Experimental Therapeutics. vol. 263, No. 1 pp. 241-245 (1992).

Ohyama et al., "Stable Expression of Natriuretic Peptide Receptors: Effects of HS-142-1, a Non-Peptide ANP Antagonist," Biochemical and Biophysical Research Communications. vol. 189, No. 1 pp. 336-342 (1992).

Plant, "Clinical use of diuretics," Clinical Medicine. vol. 3 pp. 517-520 (2003).

Potthast et al., "High Salt Intake Increases Uroguanylin Expression in Mouse Kidney," Endocrinology. vol. 142, No. 7 pp. 3087-3097 (2001).

Qian et al., "Expression of GC-C, a Receptor-Guanylate Cyclase, and Its Endogenous Ligands Uroguanyling and Guanylin along the Rostrocaudal Axis of the Intestine," Endocrinology. vol. 141, No. 9 pp. 3210-3224 (2000).

Sack, "Human Diarrheal Disease Caused by Enterotoxigenic *Escherichia coli*," Annu. Rev. Microbial. vol. 29 pp. 333-353 (1975).

Scheving, L.A., and Jin, W., "Circadian regulation of uroguanylin and guanylin in the rat intestine," Am. J. Physiol. Cell Physiol. vol. 277 pp. 1177-1183 (1999).

Schulz et al., "Guanylyl Cyclase Is a Heat-Stable Enterotoxin Receptor," Cell. vol. 63 pp. 941-948 (1990).

Shweke et al., "Tissue Transglutaminase Contributes to Interstitial Renal Fibrosis by Favoring Accumulation of Fibrillar Collagen through TGF-β Activation and Cell Infiltration," The American Journal of Pathology. vol. 173, No. 3 pp. 631-642 (2008).

Singer et al., "Contrasting endocrine response to acute oral compared with intravenous sodium loading in normal humans," Am. J. Physiol. Renal Physiol. vol. 274 pp. 111-119 (1998).

Skorecki, K.L., and Brenner, B.M., "Body Fluid Homeostasis in Man: A Contemporary Overview," The American Journal of Medicine. vol. 70 pp. 77-88 (1981).

Swenson et al., "The Guanylin/STa Receptor Is Expressed in Crypts and Apical Epithelium throughout the Mouse Intestine," Biochemical and Biophysical Research Communication, vol. 225 pp. 1009-1014 (1996).

Thomas, C.J., and Woods, R.L., "Guanylyl Cyclase Receptors Mediate Cardiopulmonary Vagal Reflex Actions of ANP," Hypertension. vol. 41 pp. 279-285 (2003).

Tsukahara et al., "Uroguanylin level in umbilical cord blood," Pediatrics International. vol. 43 pp. 267-269 (2001).

Vaandrager, "Structure and function of the heat-stable enterotoxin receptor/guanylyl cyclase C," Molecular and Cellular Biochemistry. vol. 230 pp. 73-83 (2002).

Villarreal et al., "ANF and postprandial control of sodium excretion in dogs with compensated heart failure," Am. J. Physiol Regulatory Integrative Comp. Physiol. pp. 232-239 (1990).

Vilsbøll et al., "Both GLP-1 and GIP are insulinotropic at basal and postprandial glucose levels and contribute nearly equally to the incretin effect of a meal in healthy subjects," Regulatory Peptides. vol. 114 pp. 115-121 (2003).

von Geldern et al., "Atrial Natriuretic Peptide Antagonists: Biological Evaluation and Structural Correlations," Molecular Pharmacology. vol. 38 pp. 771-778 (1990).

Hague, Kathleen L., "Summary of the Most Common Diuretics," Pulmonary Hypertension: The Complete Resource, pp. 1-3, Oct. 2002.

Arendshorst, W.J., and Beierwaites, W.H., "Renal tubular reabsorption in spontaneously hypertensive rats," American Journal of Physiology, vol. 237, pp. F38-F47 (1979).

Arendshorst, W.J., and Gottschalk, C.W., "Glomerular ultrafiltration dynamics: euvolemic and plasma volume-expanded rats," American Journal of Physiology, vol. 239 pp. F171-F186 (1980).

Boffa et al., "Thromboxane Receptor Mediates Renal Vasoconstriction and Contributes to Acute Renal Failure in Endotoxemic Mice," Journal of the American Society of Nephrology, vol. 15 pp. 2358-2365 (2004).

Cardin et al., "Portal glucose infusion increases hepatic glycogen deposition in conscious unrestrained rats," Journal of Applied Physiology, vol. 87 pp. 1470-1475 (1999).

Carrithers et al., "Guanylin and uroguanylin induce natriuresis in mice lacking guanylyl cyclase-C receptor," Kidney International. vol. 65 pp. 40-53 (2004).

Chatziantoniou et al., "Exaggerated renal vascular reactivity to angiotensin and thromboxane in young geneticallly hypertensive rats," American Journal of Physiology. vol. 259 pp. F372-F382 (1990).

Dautrey et al., "Active intestinal elimination of ciprofloxacin in rats: modulation by different substrates," British Journal of Pharmacology, vol. 127 pp. 1728-1734 (1999).

Duch et al., "Volatile anethetics significantly suppress central and peripheral mammalian sodium channels," Toxicology Letters. vol. 100-101 pp. 255-263 (1998).

Dulbecco, R., and Freeman, G., "Plaque Production by the Polyoma Virus," Virology. vol. 8 pp. 396-397 (1959).

Fields, "Solid phase peptide synthesis utilizing 9-fluorenylmethoxycarbonyl amino acids," Int. J. Pept. Protein Res. vol. 35, No. 3 pp. 161-214 (1990) [Abstract].

Fonteies et al., "Natriuretic and kaliuretic activities of guanylin and uroguanylin in the isolated perfused rat kidney," American Journal of Physiology, vol. 275 pp. F191-F197 (1998).

Forte, "A novel role for uroguanylin in the regulation of sodium balance," The Journal of Clinical Investigation. vol. 112, No. 8 pp. 1138-1141 (2003).

Fukae et al., "Changes in Urinary Levels and Renal Expression of Uroguanylin on Low or High sail Diets in Rats," Nephron, vol. 92, No. 2, pp. 373-378 (2002) [Abstract].

Fukae et al., "Plasma Concentration of Uroguanylin in Patients on Maintenance Dialysis Therapy," Nephron, vol. 84 pp. 206-210 (2000).

Goy et al., slides from "Three things to remember from John Lorenz's talk," pp. 1-67, 2010.

Huse et al., "Generation of a Large Combinatorial Library of the Immunoglobulin Repertoire on Phage Lambda,"Science. vol. 246 pp. 1275-1281 (1989).

Janknecht et al., "Rapid and efficient purification of native histidine-tagged protein expressed by recombinant vaccina virus," PNAS, vol. 88 pp. 8972-8976 (1991).

Lennane et al., "A comparison of natriuresis after oral and intravenous sodium loading in sodium-depleted man: evidence for a gastrointestinal or portal monitor of sodium intake," Clin. Sci. Mol. Med. vol. 49, No. 5 pp. 437-440 (1975) [Abstract].

Lennane et al., "A comparison on natriuresis after oral and intravenous sodium loading in sodium-depleted rabbits: evidence for a gastrointestinal or portal monitor of sodium intake," Clin. Sci. Mol. Med. vol. 49, No. 5, pp. 433-436 (1975), [Abstract].

Li et al., "Guanylin, an endogenous ligand for C-type guenylate cyclase, is produced by goblet cells in the rat intestine," Gastroenterology. vol. 109, No. 6 pp. 1863-1875 (1995) [Abstract].

Lima et al., "The effects of Escherichia coli neat-stable enterotoxin in renal sodium tubular transport," Pharmacol. Toxicol. vol. 70, No. 3 pp. 163-167 (1992) [Abstract].

Main, "When should atherematous renal artery stenosis be considered? A guide for the general physician," Clinical Medicine, vol. 3, No. 6 pp. 520-526 (2003).

Mann et al., "Mice Lacking the Guanylyl Cyclase C Receptor Are Resistant to STa-Induced Intestinal Secretion," Biochemical and Biophysical Research Communications, vol. 239 pp. 463-466 (1997).

Miyajima et al., "Expression of murine and human granulocyte—macrophage colony-stimulating factors in S. cerevisiae: mutagenesis of the potential glycosylation sites," The EMBO Journal. vol. 5, No. 6 pp. 1193-1197 (1986).

Moss et al, "Uroguanylin, an intestinal Netriuretio Peptide, Is Delivered to the Kidney as an Unprocessed Popeptide," Endocrinology. vol. 149, No. 9 pp. 4486-4498 (2008).

Perkins et al., "Uroguanylin is expressed by enterochromaffin cells in the rat gastreintestinal tract," Gastroenterology. vol. 113, No. 3 pp. 1007-1014 (1997) [Abstract].

Sastry et al., "Cloning of the immunological repertoire in Escherichia coli for generation of monoclonal catalytic antibodies: Construction of a heavy chain variable region-specific cDNA library," PNAS. vol. 86 pp. 5728-5732 (1989).

Savina et al., "Optimal Perfusion Rate Determined for In Situ Intestinal Absorption Studies in Rats," Journal of Pharmaceutical Sciences, vol. 70, No. 3 pp. 239-243 (1981).

Schück et al., "Tubular compensation for glomerular filtration rate decrease in chronic renal failure—the clinicopharmacologic point of view," Int. J. Clin. Pharmacol. Ther. Toxicol. vol. 19, No. 8 pp. 335-340 (1981) [Abstract].

Simpson, "Sodium Intake, Body Sodium, and Sodium Excretion," The Lancet, vol. 2 pp. 25-29 (1988).

Sindiće et al., "Guanylin, Uroguanyiin, and Heat-stable Euterotoxin Activate Guanylate Cyclase C and/or a Pertussis Toxin-sensitive G Protein in Human Proximal Tubule Cells," The Journal of Biological Chemistry, vol. 277, No. 20 pp. 17758-17767 (2002).

Stoupakis, G., and Klapholz, M., "Natriuretic peptides: biochemistry, physiology, and therapeutic role in heart failure," Heart Dis. vol. 5, No. 3 pp. 215-223 (2003) [Abstract].

Yusufi et al., "Differential properties of brush-border membrane vesicles from early and late proximal tubules in rat kidney," Biochimica et Biophysica Acta. vol. 1191 pp. 117-132 (1994).

Allison et al., "Renal function in chronic obstructive juandice: a micropuncture study in rats," Clinical Science and Molecular Medicine. vol. 54 pp. 649-659 (1978).

Fields, G.B., and Noble, R.L., "Solid phase peptide synthesis utilizing 9-fluorenylmethoxycarbonyl amino acids," Int. J. Peptide Protein Res. vol. 35, No. 3 pp. 161-214 (1990).

Freireich et al., "Quantitative Comparison of Toxicity of Anticancer Agents in Mouse, Rat, Hamster, Dog, Monkey, and Man," Cancer Chemtherapy Reports. vol. 50, No. 4, pp. 219-244 (1966).

Fukae et al., "Changes in Urinary Levels and Renal Expression of Uroguanylin on Low or High Salt Diets in Rats," Nephron. vol. 92, No. 2 pp. 373-378 (2002).

Lennane et al., "A comparison of natriuresis after oral and intravenous sodium loading in spdim-depieted man: evidence for a gastrointestinal or portal monitor of sodium intake," Clinical Science and Molecular Medicine. vol. 49, No. 5 pp. 437-440 (1975).

Lennane et al., "A comparison on natriuresis after oral and intravenous sodium loading in sodium-depleted rabbits: evidence for a gastrointestinal or portal monitor of sodium intake," Clinical Science and Molecular Medicine. vol. 49, No. 5 pp. 433-436 (1975).

Li et al., "Guanylin, an Endogenous Ligand for C-Type Guanylate Cyclase, Is Produced by Goblet Cells in the Rat Intestine," Gastroenterology. vol. 109, No. 6 pp. 1863-1875 (1995).

Lima et al., "The Effects of Escherichia coli Heat-sStable Enterotoxin in Renal Sodium Tubular Transport," Pharmacology and Toxicology. vol. 70, No. 3 pp. 163-167 (1992).

Merriefield, "Solid-Phase Peptide Synthesis," Advances in Enzymology. vol. 32 pp. 221-296 (1969).

Perkins et al., "Uroguanylin Is Expressed by Enterochromaffin Cells in the Rat Gastrointestinal Tract," Gastroenterology. vol. 113, No. 3 pp. 1007-1014 (1997).

Schück et al., "Tubular compensation for glomerular filtration rate decrease in chronic renal failure—the clinicopharmacologic point of view," International Journal of Clinical Pharmacology, Therapy and Toxicology. vol. 19, No. 8 pp. 335-340 (1981).

Solcia et al., "Endocrine Cells of the Digestive System," Physiology of the Gastrointestinal Tract, $2^{nd}$ Edition, Chapter 4. L.R. Johnson (ed.) Raven Press: New York, pp. 111-130 (1987).

Stoupakis, G., and Klapholz, M., "Natriuretic Peptides: Biochemistry, Physiology, and Therapeutic Role in Heart Failure," Heart Disease. vol. 5, No. 3 pp. 215-223 (2003).

* cited by examiner

```
signal peptide        2538                                                          6240            Gn₁₅
MNAWLLSVLCLLGALAVLVEGVTVQDGDLSFPLESVKQLKHLREVQEPTLMSHKKFALRLPKPVAPELCSQSAFPEALRPLCEKPNAEEILQRLEAIAQDPNTCEICAYAACTGC  proGn
MSGSQLWAAVLLLLVLQSAQGVYIKYHGFQVQLESVKKLNELEEKQMSDPQQQKSGLL-------PDVCYNPALPLDLQPVCASQEAASTFKALRTIATD--ECELCINVACTGC  proUGn
signal peptide            homology              6912       6910                                    UGn₁₆
```

*Fig. 1*

PROUROGUANYLIN, AND SYNTHETIC ANALOGS OR PROTEOLYTIC CLEAVAGE PRODUCTS DERIVED FROM IT, AS THERAPEUTIC AND DIAGNOSTIC AGENTS FOR DISEASES INVOLVING SALT AND/OR FLUID HOMEOSTASIS

CROSS REFERENCE TO RELATED APPLICATIONS

This application claims the benefit of and priority to U.S. Provisional Patent Application Ser. No. 60/571,172, filed May 14, 2004, the disclosure of which is incorporated herein by reference in its entirety.

GOVERNMENT INTEREST

This invention was made with U.S. Government support from the National Science Foundation grant number IBN-9808335 and the National Institutes of Health grant number P30-DK34987-17. The U.S. Government has certain rights in the invention.

TECHNICAL FIELD

The presently disclosed subject matter relates to methods for treating or diagnosing fluid and/or salt imbalance using prouroguanylin and/or active derivatives thereof.

ABBREVIATIONS

ACE=angiotensin converting enzyme
ANOVA=analysis of variance
ANP=atrial natriuretic peptide
ATCC=American Type Culture Collection
BSA=bovine serum albumin
° C.=degrees Celsius
cDNA=complementary DNA
cGMP=Guanosine 3',5'-cyclic monophosphate
CGN=chronic glomerular nephritis
CNP=C-type natriuretic peptide
cpm=counts per minute
CRF=chronic renal failure
DMEM=Dulbecco's minimal essential medium
DNA=deoxyribonucleic acid
dpm=disintegrations per minute
$ED_{50}$=effective dose provoking 50% of maximum response
EDTA=ethylenediaminetetraacetic acid
EC cells=enterochromaffin cells
ELISA=enzyme-linked immunosorbant assay
fmol=femtomole
GC-C=guanylyl cyclase C
GI=gastrointestinal
Gn=guanylin
HAT=hypoxanthine-aminopterin-thymidine-sensitive
HCl=hydrochloric acid
HD=hemodialysis
HEPES=4-(2-hydroxyethyl)-1-piperazineethanesulfonic acid
hr=hour
HPLC=high-pressure liquid chromatography
ip=intraperitoneal
ir-uroguanylin=immunoreactive uroguanylin
iv=intravenous
K=potassium
kDa=kilodalton
KO=knockout
LC=liquid chromatography
MALDI-TOF=matrix assisted laser desorption ionization-time of flight
MBP=maltose binding protein
min=minutes
mL=milliliter
mRNA=messenger ribonucleic acid
MS=mass spectrometry
Na=sodium
NaCl=sodium chloride
NCBI=National Center for Biotechnology Information
NLM=United States National Library of Medicine
nmol=nanomole
OMIM=Online Mendelian Inheritance in Man
PCR=polymerase chain reaction
PEG=polyethylene glycol
P.I.=preimmune
pmol=picomole
proGn=proguanylin
proUGn=prouroguanylin
rGC=receptor/guanylate cyclase
r-proUGn=recombinant prouroguanylin
RIA=radioimmunoassay
RNA=ribonucleic acid
SDS-PAGE=sodium dodecyl sulfate polyacrylamide gel electrophoresis
STa=Stable Toxin, type A
TFA=trifluoroacetic acid
UGn=uroguanylin

| AMINO ACID ABBREVIATIONS | | |
|---|---|---|
| Single-Letter Code | Three-Letter Code | Name |
| A | Ala | Alanine |
| V | Val | Valine |
| L | Leu | Leucine |
| I | Ile | Isoleucine |
| P | Pro | Proline |
| F | Phe | Phenylalanine |
| W | Trp | Tryptophan |
| M | Met | Methionine |
| G | Gly | Glycine |
| S | Ser | Serine |
| T | Thr | Threonine |
| C | Cys | Cysteine |
| Y | Tyr | Tyrosine |
| N | Asn | Asparagine |
| Q | Gln | Glutamine |
| D | Asp | Aspartic Acid |
| E | Glu | Glutamic Acid |
| K | Lys | Lysine |
| R | Arg | Arginine |
| H | His | Histidine |

BACKGROUND

Many chronic disease conditions, such as hypertension, heart failure, kidney disease and liver disease, are associated with sodium retention and/or edema. By inhibiting sodium (Na) reabsorption at different sites in the nephron, conventional diuretics help regulate sodium and fluid homeostasis to relieve edema. Several different classes of small molecule diuretics are known, including loop diuretics, such as furosemide, bumetanide, and torasemide which act in the ascending loop of Henle; thiazide-related compounds including indapamide, hydrochlorothiazide and bendroflumethiazine which act in the distal tubule; and the potassium-sparing diuretics including amiloride and triamterene which act in the cortical collecting duct. See Plant, L., *Clinical Medicine*, 3, 517-519 (2003). Many patients with hypertension or congestive heart failure, however, are unresponsive to conventional diuretics. Thus, there is a need for new treatment strategies to control the blood pressure and fluid volume in such patients, and in other subjects.

SUMMARY

The presently disclosed subject matter pertains to the diagnostic and therapeutic use of prouroguanylin (proUGn) itself, as well as fragments and/or analogs of proUGn, including any of its metabolites and chemical derivatives (distinct from a C-terminal fragment previously identified as $UGn_{18}$ in rats, and as $UGn_{16}$ in humans).

In some embodiments, the presently disclosed subject matter provides a method for treating a disorder characterized by salt retention, fluid retention, and combinations thereof, in a patient in need thereof, the method comprising administering an effective amount of prouroguanylin, or fragment or analog thereof, to the patient.

In some embodiments, the presently disclosed subject matter provides a method for determining the presence of or the progression of a disorder characterized by salt retention, fluid retention, salt loss, fluid loss, and combinations thereof, in a patient, the method comprising detecting a level of prouroguanylin in a sample (in some embodiments a plasma sample) from the patient. In some embodiments, the detecting of a level of prouroguanylin is by immunoassay.

In some embodiments, the presently disclosed subject matter provides an immunoassay kit for detecting a level of prouroguanylin in a sample.

Thus, it is an object of the presently disclosed subject matter to provide a method for treating a disorder characterized by salt retention, fluid retention, and combinations thereof. It is another object of the presently disclosed subject matter to provide a method for determining the presence of or the progression of a disorder characterized by salt retention, fluid retention, salt loss, fluid loss, and combinations thereof. It is another object of the presently disclosed subject matter to provide an immunoassay kit for detecting a level of prouroguanylin in a sample.

Certain objects of the presently disclosed subject matter having been stated herein above, which are addressed in whole or in part by the presently disclosed subject matter, other objects and aspects will become evident as the description proceeds when taken in connection with the accompanying Examples as best described herein below.

BRIEF DESCRIPTION OF THE DRAWINGS

FIG. 1 shows the amino acid sequences of rat proGn (SEQ ID NO: 9, upper sequence, cloned by Currie, M. G., et al., *Proc. Natl. Acad. Sci. U.S.A.*, 89, 947-951 (1992)) and rat proUGn (SEQ ID No: 8, lower sequence, cloned by Li Z., et al., *Regul. Pept.*, 68, 45-56 (1997)).

FIG. 2a is the HPLC elution/$T_{84}$ cell response (pmol cGMP/well) profile of a rat duodenal extract. Solid symbols correspond to fraction $T_{84}$ cell activity prior to proteolysis and open symbols correspond to fraction $T_{84}$ cell activity after proteolysis. The dashed line corresponds to the % acetonitrile in the HPLC eluant. Reproduced from Li, Z. et al., *Regul. Pept.*, 68, 45-56 (1997). FIG. 2b is a bar graph depicting the net cGMP response (stimulated-basal) of $T_{84}$ cells to HPLC fractions 44-49 from FIG. 2a before proteolysis and after proteolysis. Reproduced from Li, Z., et al., *Regul. Pept.*, 68, 45-56 (1997).

FIG. 3a is an autoradiogram of an SDS gel showing the immunoprecipitation of radiolabeled proUGn by antibodies 6910 and 6912. Molecular weight markers are indicated by the tick marks to the left of the autoradiogram. Sizes of molecular weight markers are indicated to the left, in kDa. FIG. 3b shows a Western blot of anti-proUGn antibodies 6910 and 6912 and the proteins they detect in extracts of rat small intestine. FIG. 3c shows the HPLC chromatogram of radiolabeled proUGn, with scintillation counting levels (dpm×$10^{-3}$/fraction) of the individual fractions shown in the solid symbols. The inset shows Western blots with antibody 6910, revealing the presence of a proUGn-like 8.5 kDa protein in comparable fractions of an HPLC of rat small intestine. FIG. 3d shows a Western blot using the anti-proUGn antibodies (6910 and 6912) and an anti-proGn antibody (2538) and their ability (2538) or failure (6910, 6912) to recognize a sample of recombinant proGn.

FIG. 5a shows a schematic summarizing the differences in cellular localization and vectorial secretion of proUGn and proGn. FIG. 5b is a Western blot showing recognition of plasma proUGn by anti-proUGn antibody. Plasma was fractionated by HPLC prior to immunoblotting and the numbers above the blot indicate the HPLC fraction being tested. The lane marked "std" indicates an authentic sample of proUGn. FIG. 5c is a Western blot of HPLC plasma fractions and their analysis with anti-proGn antibody. The lane marked "std" contains authentic proGn. FIG. 5d shows an HPLC chromatogram, wherein a reverse-phase column is replaced with an HPLC size-exclusion column, which provides better separation between proUGn and other abundant plasma proteins, such as albumin and immunoglobulins, and a Western blot in which removal of these interfering proteins improves the resolution of the Western blot procedure.

FIG. 6a shows a dilution series of r-proUGn tested with two different antibodies (6910 and 6912). FIG. 6b shows an immunoassay performed in triplicate using antibody 6910. The standards and unknowns (60 µg total protein isolated from three regions of the rat intestine, i.e., colon, distal ileum, and proximal jejunum, as indicated) were quantified on a LiCor ODYSSEY™ infrared imaging system. The line was fit to the standards by linear regression, and the values of the unknowns were determined by interpolation. Before analysis in this immunoassay, plasma samples must be pre-fractionated, to separate proUGn from abundant interfering plasma proteins such as albumin. The pre-fractionation is performed on an Amersham Hi-prep sephacryl S200 HR column (16 cm diameter, 60 cm length) eluted with 0.05 M sodium phosphate+0.15 M sodium chloride, pH=7 at a flow rate of 0.5 mL/min. The proUGn elutes between 135 and 155 min.

FIG. 7a shows that in the acute model, orogastric salt (3 mL of 300 mM NaCl) was delivered to anesthetized animals by gavage at 30 min. Levels of plasma proUGn, measured at 30 minutes ("before" stomach loading) and at 100 minutes ("after" stomach loading), approximately doubled in response to the solute load (n=3). FIG. 7b shows that in the chronic model, conscious rats were shifted from 0.5% to 2% dietary salt (change intake), whereupon their urinary salt excretion increased to a new steady-state level over 12 hours. Again, this was associated with an approximate doubling of plasma proUGn levels in the "high" salt intake compared to "control" salt intake (n=4). FIG. 7c shows jejunal uroguanylin mRNA expression in animals maintained for 6 days on "high" and "low" salt diets (p<0.03 paired t-test). Uroguanylin mRNA was measured by Northern blotting and normalized to β-actin mRNA levels.

FIG. 8a shows that steady infusion of $^{35}$S-proUGn over 60 minutes generates a stable plasma level of radioactivity (solid circles). Excreted levels in the urine are much greater over the same period (open circles). FIG. 8b shows that at the end of a 60-minute infusion, specific activity of labeling in the kidney is greater than in any other tissue. Abbreviations: Brain (B), thymus (T), lung (Lu), small intestine (SI), skeletal muscle (M), spleen (S), heart (H), kidney (K), liver (Li). FIG. 8c shows that a bolus dose of $^{35}$S-proUGn is cleared rapidly from the plasma of a normal animal (control; open circles), and much more slowly after renal ablation (anephric; solid circles).

FIG. 9a shows the HPLC analysis of plasma collected after bolus injection, wherein the plasma samples were taken 2 min (solid circle), 5 min (shaded circle), and 10 min (open circle) after injecting a bolus dose of 35S-labeled proUGn into the carotoid artery (n=2 for each timepoint). FIG. 9b shows the HPLC analysis of urine collected after prolonged infusion, wherein the urine was collected for 30 minutes at the end of a 60-minute arterial infusion (n=7). The cpm/μL in the infused material was approximately 100 times lower than the cpm/μL in the solution used for the bolus injection. Plasma and urine samples were applied to a Vydac 218TP C-18 reverse phase column and eluted with a gradient of acetonitrile (dashed line). Radioactivity in each HPLC fraction was measured in a scintillation counter. Retention times of Cys, Met, and proUGn standards are marked by the arrows. Metabolites derived from proUGn are indicated by the question marks in FIG. 9b.

FIG. 10a shows the UV absorbance profile of the final step in the purification of native proUGn from a rat intestinal extract. The inset shows a Western blot of individual fractions to confirm the location of proUGn (marked by the arrow). Fraction 40 was dried, resuspended in the physiological saline, and used for infusion studies, as shown in FIGS. 10b and 10c. FIG. 10b shows the time courses of blood pressure (above the dotted line) and urine production (below the dotted line) in control animals (open circles, n=5), animals infused with purified proUGn (solid circles, n=5), an animal infused with immuno-neutralized proUGn (triangles), or an animal infused with STa (squares). Agents were added to the infusate only during the interval indicated by the horizontal bar. FIG. 10c shows time courses of urinary sodium excretion (below dotted line), measured in the same experiments shown in FIG. 10b. The Western blot inset (above the dotted line) shows urinary proUGn excretion. Each sample represents 50% of the total urine collected over a 20-minute period before, during, and after peptide infusion from a representative animal: control animals (open circles, n=5), animals infused with purified proUGn (solid circles, n=5), an animal infused with immuno-neutralized proUGn (triangles), or an animal infused with STa (squares).

FIG. 11a shows the disappearance of $^{35}$S-proUGn from plasma, wherein circulating anti-proUGn antibodies slow the rate at which bolus-injected $^{35}$S-proUGn disappears from plasma: acute Ab block (solid circles); 24-hr chronic Ab block (shaded circle); and nonimmune serum (open circle). FIG. 11b shows the excretion of proUGn metabolites into urine: control (solid bar) and acute Ab block (open bar), wherein circulating anti-proUGn antibodies attenuates urinary excretion of labeled metabolites after bolus injection of $^{35}$S-proUGn into plasma. FIG. 11c shows Na excretion into urine after gastric load, wherein circulating anti-proUGn antibodies inhibit Na excretion evoked by an orogastric Na: nonimmune serum (open circles) and acute Ab block (solid circles).

BRIEF DESCRIPTION OF THE SEQUENCES IN THE SEQUENCE LISTING

Figure 2:
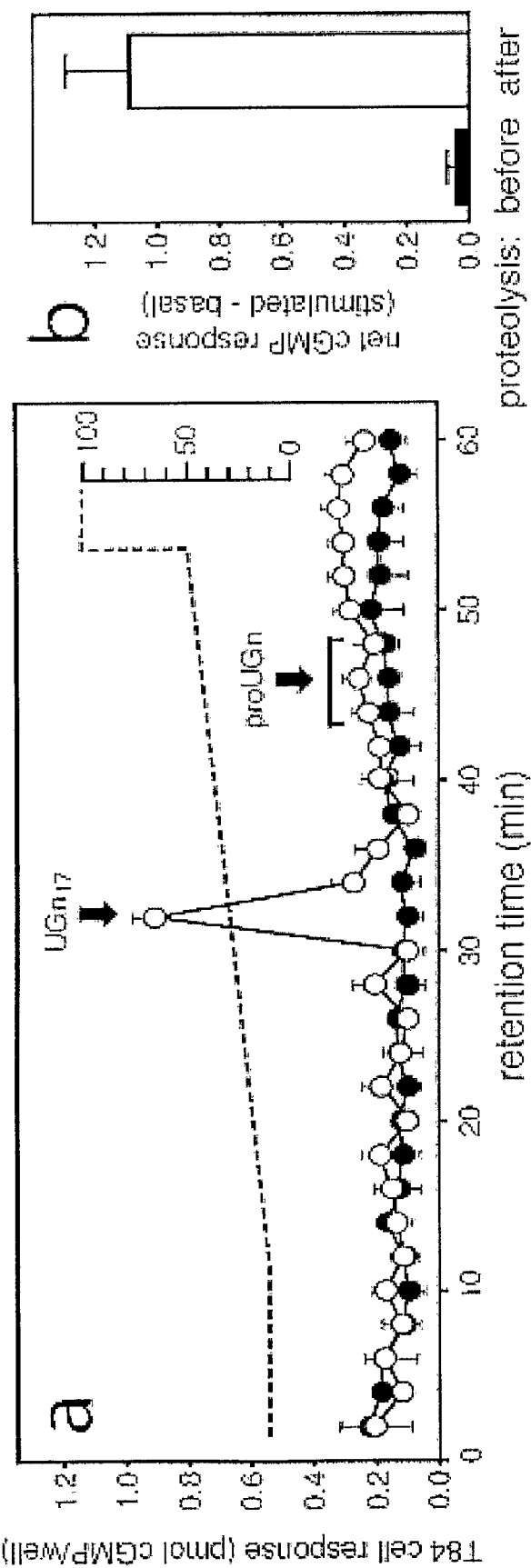
FIGS. 2a and 2b show the activity of rat intestinal extract on $T_{84}$ cells.

SEQ ID NO: 1 is an amino acid sequence for rat $UGn_{18}$.

SEQ ID NO: 2 is an amino acid sequence for human $UGn_{16}$.

SEQ ID NO: 3 is an amino acid sequence for rat pre-prouroguanylin.

SEQ ID NO: 4 is an amino acid sequence for human pre-prouroguanylin.

SEQ ID NO: 5 is an amino acid sequence for human prouroguanylin.

SEQ ID NO: 6 is an amino acid sequence for rat $Gn_{15}$.

SEQ ID NO: 7 is an amino acid sequence for the immunogen used to raise the polyclonal anti-proUGn antibody 6910.

SEQ ID NO: 8 is an amino acid sequence for rat prouroguanylin cloned by Li Z., et al., *Regul. Pept.*, 68, 45-56 (1997)).

SEQ ID NO: 9 is an amino acid sequence for rat proguanylin cloned by Currie, M. G., et al., *Proc. Natl. Acad. Sci. U.S.A.*, 89, 947-951 (1992))

SEQ ID NO: 10 is an amino acid sequence for the immunogen used to raise the polyclonal anti-proUGn antibody 6912.

SEQ ID NO: 11 is an amino acid sequence for the immunogen used to raise the polyclonal anti-proGn antibody 2538.

SEQ ID NO: 12 is an amino acid sequence for the immunogen used to raise the polyclonal anti-proGn antibody 6240.

DETAILED DESCRIPTION

The presently disclosed subject matter pertains, in part, to the following aspects: (I) the diuretic and natriuretic effects of infused prouroguanylin (proUGn), or its derivatives are a benefit to patients, e.g., human patients, suffering from diseases that lead to derangements of salt and/or fluid homeostasis, including patients with hypertension, heart disease, kidney disease, or liver disease, as well as patients who are not responsive to conventional diuretics; and (II) measuring the plasma levels of endogenous proUGn (and/or the ratio of endogenous proUGn to endogenous $UGn_{18}$ in rats, and as $UGn_{16}$ in humans) is of diagnostic value in evaluating the status of patients with such diseases.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

Following long-standing patent law convention, the terms "a" and "an" mean "one or more" when used in this application, including the claims.

As used herein, the term "diuretic" refers to a compound that increases the rate of urine formation. As used herein, the term "natriuretic" refers to a compound that increases the rate of urinary sodium excretion. Thus, as used herein, the term "diuresis" refers to an increase in fluid excretion and the term "natriuresis" refers to an increase in sodium excretion.

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein, refers to peptides, polypeptides and proteins, unless otherwise noted. As used herein, the terms "protein," "polypeptide" and "peptide" are used interchangeably herein when referring to a gene product.

As used herein, the terms "$UGn_{18}$" (in rats) or "$UGn_{16}$" (in humans) refer to the peptide derived from the C-terminal domain of prouroguanylin, which can contain anywhere from 15 to 20 amino acids, including 15, 16, 17, 18, 19, and/or 20 amino acids. These peptides are potent activators of guanylyl cyclase C (GC-C), a receptor/guanylyl cyclase that is responsible for ligand-activated cGMP synthesis in the intestinal epithelium. The rat sequence, TIATDECELCINVACTGC (SEQ ID NO: 1) has been previously published. See Li, Z., et al., *Reg. Peptides,* 68, 45-56 (1997). A reference for a human sequence, NDDCELCVNVACTGCL (SEQ ID NO: 2) is: Kita, T., et al., *Am. J. Physiol.,* 266, F342-F348 (1994). As used herein, the term "uroguanylin" will be used when it is not useful (or not possible) to make a distinction between the propeptide and the guanylyl cyclase C (GC-C)-activating peptide. As used herein, the terms "prouroguanylin" and "proUGn" refer to the propeptide of $UGn_{18}$ in rats, and as $UGn_{16}$ in humans and can be used interchangeably.

Rat preprouroguanylin as purified and sequenced by Li Z., et al., *Regul. Pept.,* 68, 45-56 (1997)) has the amino acid sequence: MSGSQLWAAVLLLLVLQSAQGVYIKYHG-FQVQLESVKKLNELEEKQMSDPQ QQKSGLLPDV-CYNPALPLDLQPVCASQEAASTFKALR-TIATDECELCINVACT GC (SEQ ID NO: 3). The signal sequence is shown in italics and the $UGn_{18}$ is shown in bold. Removal of the signal peptide, which usually occurs automatically as the prepropeptide is being made, gives rise to prouroguanylin.

Human preprouroguanylin has the amino acid sequence: MGCRAASGLLPGVAVVLLLLLQSTQS-VYIQYQGFRVQLESM KKLSDLEAQWA PSPRLQAQS-LLPAVCHHPALPQDLQPVCASQEAS-SIFKTLRTIANDDCELCVN VACTGCL (SEQ ID NO: 4). The signal sequence is shown in italics and the $UGn_{16}$ is shown in bold. In humans, the active C-terminal form of the peptide was purified from urine (not the intestine), and it actually has a slightly shorter sequence comprised of only 16 amino acid residues (again bold above, and reported in Kita, T., et al., *Am. J. Physiol.,* 266, F342-F348 (1994)). Thus, human $UGn_{16}$ is "comparable" to rat $UGn_{18}$.

Human prouroguanylin has the amino acid sequence: VYIQYQGFRVQLESMKKLSDLE-AQWAPSPRLQAQSLLPAVCHHPALPQDLQP VCASQE-ASSIFKTLRTIANDDCELCVNVACTGCL (SEQ ID NO: 5).

As used herein, the term "$Gn_{15}$" refers to the C-terminal sequence of proguanylin that activates GC-C. Rat $Gn_{15}$ has the sequence PNTCEICAYAACTGC (SEQ ID NO: 6). The terms "proguanylin" and "proGn" refer to the propeptide of $Gn_{15}$ and can be used interchangeably. The term "guanylin" will be used when it is not useful (or not possible) to make a distinction between the propeptide and the GC-C activating peptide.

As used herein, the term "fragment" refers to a peptide or protein having an amino acid sequence shorter than that of the amino acid sequence of the entire reference peptide or protein. Such a fragment can be a metabolite or a proteolytic fragment. As used herein, the terms "metabolite" and "proteolytic fragment" refer to peptide fragments that are produced through the action of enzymes (for example, proteases, etc.) or other processes that occur in vivo, or that are implemented in vitro or in another setting. Fragments also can be chemically synthesized or recombinantly produced peptide or protein sequences. Fragments also can be produced by enzymatic processes in vitro.

In some embodiments of the presently disclosed subject matter an effective amount of a "renal metabolite" of prouroguanylin having diuretic activity is administered to a patient in need of treatment. As used herein, a "renal metabolite of prouroguanylin" refers to a metabolite produced from the biological degradation of the propeptide in the kidney (in some embodiments from the brush border proteases present in proximal tubule), wherein the metabolite is not $UGn_{18}$ in rats, and as $UGn_{16}$ in humans.

As used herein, the term peptide "analog" refers to a peptide that contains one or more structural modifications relative to the native peptide or protein. Such modifications can refer to the addition or deletion of one or more amino acid groups in the peptide sequence. Modifications also can relate to altered stereochemistry, for example the inclusion of one or more D-amino acids in place of the native L-amino acid. Modifications also can include the addition of non-peptide groups which can include groups for aiding in the detection of a peptide or protein, such as a radiolabelling component or a fluorescent moiety, groups that can alter the solubility of the peptide or protein, such as fatty acid groups, carbohydrates, or polymer groups, or groups that can protect the peptide or protein from enzymatic degradation.

The terms "fragment" and "analog," as provided hereinabove, can encompass metabolites and chemical derivatives.

As used herein, the term "expression" generally refers to the cellular processes by which a polypeptide is produced from RNA.

As used herein, the term "labeled" means the attachment of a moiety, capable of detection by spectroscopic, radiologic or other methods, to a probe molecule.

As used herein, the term "mutation" carries its traditional connotation and means a change, inherited, naturally occurring or introduced, in a nucleic acid or polypeptide sequence, and is used in its sense as generally known to those of skill in the art.

The term "postprandial natriuresis" is used to describe the entire renal natriuretic response to orogastric salt intake. The term "entero-renal axis" is used to describe the specific component of this response that originates in the intestine.

As used herein, the terms "effective amount" and "therapeutically effective amount" are used interchangeably and mean a dosage sufficient to provide treatment for the disease state being treated. This dosage can vary depending on the patient, the disease and the treatment being effected.

In some embodiments, the effective amount of prouroguanylin, or fragment or analog thereof, is administered in combination with one or more other drugs that affect salt balance, fluid balance, or both salt and fluid balance. The term "in combination" can refer to the administration of active agents in a single composition or in one or more separate compositions.

The term "about," as used herein, when referring to a value or to an amount of mass, weight, time, volume, or percentage is meant to encompass variations of ±20% or ±10%, more preferably ±5%, even more preferably ±1%, and still more preferably ±0.1% from the specified amount, as such variations are appropriate to perform the disclosed method.

The patient treated in the many embodiments disclosed herein is desirably a human patient, although it is to be understood that the principles of the presently disclosed subject matter indicate that the presently disclosed subject matter is effective with respect to all vertebrate species, including mammals, which are intended to be included in the term "patient." In this context, a mammal is understood to include any mammalian species in which treatment is desirable, particularly agricultural and domestic mammalian species, such as horses, cows, pigs, dogs, and cats.

II. General Considerations

II.A. Uroquanylin and Guanylin

The identification of $UGn_{18}$ and proUGn began as an outgrowth of a clinical problem related to intestinal electrolyte handling. Pathogenic strains of *E. coli* produce a toxin (STa) that causes diarrheal disease by binding to a receptor expressed on the apical surfaces of epithelia cells. See Sack, R. B., *Annu. Rev. Microbiol.*, 29, 333-353 (1975). Receptor activation stimulates cGMP synthesis, which activates CFTR chloride channels and inhibits Na/H exchange, leading to uncontrollable accumulation of water and electrolytes in the intestinal lumen. See Vaandrager, A. B., *Mol. Cell Biochem.*, 230, 73-83 (2002). In 1990, the receptor for STa was cloned and shown to be a member of a family of receptor/guanylate cyclases (rGCs). See Schultz, S., et al., *Cell*, 63, 941-948 (1990). As the third member of this family, the STa receptor was named guanylate cyclase-C, or GC-C.

Other members of the rGC family (GC-A and GC-B) are receptors for natriuretic peptides—GC-A for the atrial natriuretic peptide (ANP) and GC-B for the C-type natriuretic peptide (CNP). See Kuhn, M., *Circ. Res.*, 93, 700-709 (2003); Koller, K. J., *Science*, 252, 120-123 (1991). It was therefore widely speculated that an endogenous ligand would ultimately be found to activate GC-C in a physiological context (in contrast to pathological activation by STa). This expectation was fulfilled when two GC-C-activating ligands—a 15 amino acid peptide called guanylin ($Gn_{15}$) and an 18 amino acid peptide called uroguanylin ($UGn_{18}$)—were purified from urine and intestinal extracts. See Currie, M. G., et al., *Proc. Natl. Acad. Sci.*, 89, 947-951 (1992); Hamra, F. K., et al., *Proc. Natl. Acad. Sci.*, 90, 10464-10468 (1993); Li, Z., et al., *Regul. Pept.*, 68, 45-56 (1997); U.S. Pat. No. 5,489,670 to Currie et al.; U.S. Pat. No. 5,879,656 to Waldman. As noted above, in humans, the active C-terminal form of the peptide was purified from urine (not the intestine), and it actually has a slightly shorter sequence comprised of only 16 amino acid residues. Thus, human $UGn_{16}$ is "comparable" to rat $UGn_{18}$.

II.B. Prouroquanylin and Proquanylin

The $Gn_{15}$ and $UGn_{18}$ sequences are found at the C-termini of precursor propeptides-proguanylin and prouroguanylin, respectively. Prouroguanylin and proguanylin share several structural features (see FIG. 1) including signal peptides at their N-termini, homology at their C-termini where the $Gn_{15}$ and $UGn_{18}$ sequences are located, and a short region of homology (but unknown function) adjacent to their signal peptides. Outside of these regions, the sequences of the two propeptides are relatively poorly conserved.

Sequences for proUGn have been published for a number of species, including human, pig, rat, mouse, opossum and guinea pig. See Hidaka, Y., et al., *J. Biol. Chem.*, 275, 25155-25162 (2000). ProUGn and proGn are expressed almost exclusively in the intestine (although small amounts of proUGn polypeptide also are found in the kidney), with each propeptide being produced by a different type of intestinal cell. See Perkins, A., et al., *Gastroenterology*, 113, 1007-1014 (1997); Qian, X., et al., *Endocrinology*, 141, 3210-3224 (2000); Li., Z, et al., *Gastroenterology*, 109, 1863-1875 (1995).

ProGn is produced by goblet cells, mostly in the distal small intestine and the colon. See Qian, X., et al., *Endocrinology*, 141, 3210-3224 (2000); Li, Z., et al., Gastroenterology, 109, 1863-1875 (1995). Goblet cells are better known as the source of mucin, a glycoprotein that is secreted into the intestinal lumen, where if forms a mucus gel by absorbing water and electrolytes. Consistent with the exocrine nature of mucin secretion, a study of isolated intraluminally and vascularly perfused colon found that guanylin (recovered mostly as $Gn_{15}$) also is preferentially secreted into the lumen, with a lumen-to-plasma ratio in excess of 40-fold. See Moro, F., et al., *Endocrinology*, 141, 2594-2599 (2000); Martin, S., et al., *Endocrinology*, 140, 5022-5029 (1999). These observations have led to the proposal that guanylin plays a role in the hydration of mucin, particularly in the relatively dehydrated distal intestine, by providing close spatial and temporal linkage between mucin release and $Gn_{15}$-induced fluid movement. See Qian, X., et al., *Endocrinology*, 141, 3210-3224 (2000); Li, Z., et al., *Gastroenterology*, 109, 1863-1875 (1995); Cohen, M. B., et al., *Biochem. Biophys. Res. Commun.*, 209, 803-808 (1995).

In contrast, enteric proUGn is produced by enterochromaffin (EC) cells, almost exclusively within the small intestine. See Perkins, A., et al., *Gastroenterology*, 113, 1007-1014 (1997); Li, Z., et al., *Regul. Pept.*, 68, 45-56 (1997); Mivazato, M., et al., *FEBS Lett.*, 398, 170-174 (1996). EC cells are one of the most abundant endocrine cells in the GI tract. They contain serotonin, usually along with one or more peptides. See Solcia, E., et al., Endocrine Cells in the Digestive System, in *Physiology of the Gastrointestinal Tract* (L. R. Johnson, ed., Raven Press, New York, 1987), 111-130. EC cells release serotonin (and presumably co-localized peptides) both basolaterally, and apically, though basolateral secretion predominates. See Nilsson, O., et al., *Cell Tissue Res.*, 248, 49-54 (1987).

Although the propeptides are expressed in intestinal tissue, the same tissues appear to contain little $UGn_{18}$ or $Gn_{15}$. $UGn_{18}$ and $Gn_{15}$ are too small to detect by immunoblotting. Instead, they usually are measured either by standard RIA methods, or (more commonly) by bioassay, using a "reporter cell"—the colon-carcinoma-derived $T_{84}$ cell line—that expresses high levels of GC-C, and therefore synthesizes cGMP when exposed to GC-C-activating ligands. Guarino, A., et al., *Am. J. Physiol.*, 253, G775-G780 (1987); Dharmsathaphorn, K., et al., *Am. J. Physiol.*, 246, G204-G208 (1984). Somewhat surprisingly, aqueous extracts of small or large intestine fail to induce a cGMP response in $T_{84}$ cells unless the extracts have been pretreated with a protease. See Li, Z., et al., *Regul. Pept.*, 68, 45-56 (1997). For example, as illustrated in FIG. 2a, all of the HPLC fractions derived from a rat duodenal extract are initially inactive when tested in the reporter cell assay (solid symbols); however, fractions 44-49 (spanning the retention time of proUGn) can be activated by proteolysis (FIG. 2b), and when the activated material is rechromatographed, its retention time now shifts to an earlier point in the chromatogram, corresponding to the retention time of $UGn_{18}$ (FIG. 2a, open symbols). This finding is consistent with other reports of the inability of proUGn and proGn to activate GC-C. See Hamra, F. K., et al., *Endocrinology*, 137, 257-265 (1996). Because extracts of intestinal tissue contain very little $Gn_{15}$ and $UGn_{18}$, processing is assumed to occur after secretion of the propeptides.

II.C. The Entero-Renal Axis and Uroquanylin

In the search for new types of diuretic agents, one area of research has focused on determining the link between the intestine's response to sodium intake and the kidney. An entero-renal endocrine axis involved in the regulation of solute excretion was first proposed in the 1970's. See Lennane, R. J., et al., *Clin. Sci. Mol. Med.*, 49, 433-436 (1975). Any change in extracellular Na content (produced, for example, by oral ingestion of salt) initiates thirst and antidiuretic hormone mechanisms, which evoke compensatory changes in extracellular fluid volume. See Skorecki, K. L. and Brenner, B. M., *Am. J. Med.*, 70, 77-88 (1981). Extracellular volume, however, responds slowly to alterations in salt intake and hours or days can be required to establish a new equilibrium between Na intake and urinary output. See Carey, R. M., *Circ. Res.*, 43, 19-23 (1978); Simpson, F. O., *Lancet*, 2, 25-29 (1988). A rapid entero-renal reflex, sometimes referred to as the postprandial natriuretic response (see Ise, T., et al., *Kidney Int. Suppl.*, 67, S245-S249 (1998); Villarreal, D., et al., *Am. J. Physiol.*, 258, R232-R239 (1990)), is demonstrated in the fact that when matched solute loads are delivered orally and intravenously, natriuresis is evoked more rapidly with oral delivery. See Lennane, R. J., et al., *Clin. Sci. Mol. Med.*, 49, 433-436 (1975); Singer, D. R., et al., *Am. J. Physiol.*, 274, F111-F119 (1998); Mu, J., et al., *Pflugers Arch.*, 438, 159-164 (1999).

The mechanism of this entero-renal axis is still under active investigation. Two models have been proposed: a direct mechanism, in which a natriuretic factor is released from the gut in response to an intraluminal stimulus; and an indirect mechanism, in which a signal from the gut initiates the release of a natriuretic factor from another site. The indirect mechanism has most often been associated with hepatic afferent nerves that respond to salt levels in the portal vein and are thought to initiate a reflex natriuresis through alterations in renal nerve activity, or, perhaps, by the release of natriuretic agents from a central or peripheral location. See Nishida, Y., et al., *Am. J. Physiol.*, 274, R97-R103 (1998); Haberle, D. A., et al., *Kidney Int. Suppl.*, 67, S242-S244 (1998). In recent years, a case also has been made for the direct mechanism, in which natriuresis is induced in the kidney by a peptide released from the gut in response to Na intake.

III. Peptide, Polypeptide and Polynucleotide Components of the Presently Disclosed Subject Matter The following section discloses a plurality of molecules that can form an aspect of the presently disclosed subject matter. This discussion is not meant, however, to be an inclusive list of molecules that can form an aspect of the presently disclosed subject matter. Biological information, including nucleotide and peptide sequence information, with regard to the presently disclosed peptide, polypeptide, and polynucleotide molecules is available from public databases provided, for example, by the National Center for Biotechnology Information (NCBI) located at the United States National Library of Medicine (NLM). The NCBI is located on the World Wide Web at ncbi.nlm.nih.gov and the NLM is located on the World Wide Web at nlm.nih.gov. The NCBI website provides access to a number of scientific database resources including: GenBank, PubMed, Genomes, LocusLink, Online Mendelian Inheritance in Man (OMIM), Proteins, and Structures. A common interface to the polypeptide and polynucleotide databases is referred to as Entrez which can be accessed from the NCBI website or through the LocusLink website.

The amino acid sequences of prouroguanylin and of preprouroguanylin are known in the art, as described hereinabove. The presently disclosed subject matter provides for the use of human prouroguanylin, as well as homologous prouroguanylins, including bovine, porcine, equine, canine, and other mammalian prouroguanylins. In some embodiments, it is envisioned that preprouroguanylin can be employed, and thus, as used herein with reference to disclosed methods and techniques the term "prouroguanylin" includes "preprouroguanylin". The presently disclosed subject matter also provides for the use of fragments of prouroguanylin, such as fragments that can be provided by proteolytic cleavage of prouroguanylin in the subject or outside the subject prior to administering the fragments. In some embodiments, the prouroguanylin fragments can be modified in accordance with art-recognized techniques to be resistant to further degradation. Such techniques can include, but are not limited to, including an amino acid sequence in the fragment that is resistant to degradation.

In some embodiments, the presently disclosed subject matter discloses the use of renal metabolites of prouroguanylin having diuretic and/or natriuretic activity. As provided hereinabove, a "renal metabolite of prouroguanylin" refers to a metabolite produced from the biological degradation of the propeptide in the kidney (for example, in some embodiments from the brush border proteases present in proximal tubule), under the proviso that the metabolite is not $UGn_{18}$ in rats, and as $UGn_{16}$ in humans. Methods for determining the amino acid sequences of prouroguanylin renal metabolites are discussed herein below in the examples.

The presently disclosed subject matter also describes the use of polypeptides that have a sequence substantially identical to prouroguanylin and/or prouroguanylin fragments, e.g., prouroguanylin analogs. A polypeptide which is "substantially identical" to a given reference polypeptide is a polypeptide having a sequence that has at least 85% identity to the sequence of the given reference polypeptide sequence. Substantially identical polypeptides also can have a higher percentage identity, e.g., 90%, 95%, 98%, or 99%. The presently disclosed subject matter also encompasses polypeptides that are functionally equivalent to prouroguanylin and/or prouroguanylin fragments. These polypeptides are equivalent to prouroguanylin and/or prouroguanylin fragments in that they are capable of carrying out one or more of the functions of prouroguanylin and/or prouroguanylin fragments in a biological system. Such polypeptides have 60%, 75%, 80%, or even 90% of one or more of the biological activities of full-length prouroguanylin and/or prouroguanylin fragments. Such comparisons are generally based on an assay of biological activity in which equal concentrations of the polypeptides are used and compared. The comparison also can be based on the amount of the polypeptide required to reach 50% of the maximal activity obtainable.

Functionally equivalent polypeptides can be those, for example, that contain additional or substituted amino acid residues. Substitutions can be made on the basis of similarity in polarity, charge, solubility, hydrophobicity, hydrophilicity, and/or the amphipathic nature of the residues involved. For example, a functionally equivalent polypeptide is one in which 10% or fewer of the amino acids full-length, naturally occurring prouroguanylin and/or prouroguanylin fragments are replaced by conservative amino acid substitutions, and the functionally equivalent polypeptide maintains at least 50% of the biological activity of full-length prouroguanylin and/or prouroguanylin fragments.

Conservative amino acid substitution refers to the substitution of one amino acid for another amino acid of the same class (e.g., valine for glycine, or arginine for lysine). Polypeptides that are functionally equivalent to prouroguanylin and/or prouroguanylin fragments can be made using random mutagenesis on the encoding nucleic acids by techniques well known to those having ordinary skill in the art. It is more likely, however, that such polypeptides will be generated by site-directed mutagenesis (again using techniques well known to those having ordinary skill in the art). These polypeptides can have increased functionality or decreased functionality.

To design functionally equivalent polypeptides, it is useful to distinguish between conserved positions and variable positions. This distinction can be accomplished by aligning the amino acid sequence of a protein of the presently disclosed subject matter from one species with its homolog from another species. Skilled artisans will recognize that conserved amino acid residues are more likely to be necessary for preservation of function. Thus, it is preferable that conserved residues are not altered.

Mutations within the coding sequence of a nucleic acid molecule encoding prouroguanylin and/or prouroguanylin fragments can be made to generate variant genes that are better suited for expression in a selected host cell. For example, N-linked glycosylation sites can be altered or eliminated to achieve, for example, expression of a homogeneous product that is more easily recovered and purified from yeast hosts that are known to hyperglycosylate N-linked sites. To this end, a variety of amino acid substitutions at one or both of the first or third amino acid positions of any one or more of the glycosylation recognition sequences which occur, and/or an amino acid deletion at the second position of any one or more of such recognition sequences, will prevent glycosylation at the modified tripeptide sequence (see, e.g., Miyajima et al., *EMBO J.*, 5, 1193 (1986)).

The prouroguanylin and/or polypeptide prouroguanylin analogs and/or prouroguanylin fragments and/or prouroguanylin fragment analogs used in accordance with the presently disclosed subject matter can be expressed fused to another polypeptide, for example, a marker polypeptide or fusion partner. For example, the polypeptide can be fused to a hexahistidine tag to facilitate purification of bacterially expressed protein or a hemagglutinin tag to facilitate purification of protein expressed in eukaryotic cells. A fusion protein can be readily purified by utilizing an antibody specific for the fusion protein being expressed. For example, a system described by Janknecht et al. allows for the ready purification of non-denatured fusion proteins expressed in human cell lines (*Proc. Natl. Acad. Sci. USA,* 88: 8972-8976 (1991)). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitrilo-acetic acid-agarose columns and histidine-tagged proteins are selectively eluted with imidazole-containing buffers.

The prouroguanylin and/or polypeptide prouroguanylin analogs and/or prouroguanylin fragments and/or prouroguanylin fragment analogs used as components of the presently disclosed subject matter also can be chemically synthesized and/or chemically modified (for example, see Creighton, *Proteins: Structures and Molecular Principles*, W.H. Freeman & Co., NY, 1983), or, perhaps more advantageously for larger peptides, produced by recombinant DNA technology as described herein. For additional guidance, skilled artisans can consult Ausubel, F. M., et al., *Protocols in Molecular Biology*, New York: Greene Publishing Associates and John Wiley & Sons, 1992; Sambrook et al., *Molecular Cloning, A Laboratory Manual*, Cold Spring Harbor Press, Cold Spring Harbor, N.Y. (1989).

Synthetic chemistry techniques, such as a solid-phase Merrifield-type synthesis, are preferred for smaller peptides for reasons of purity, antigenic specificity, freedom from undesired side products, ease of production and the like. A summary of many available techniques can be found in Steward et al., *Solid Phase Peptide Synthesis*, W. H. Freeman Co., San Francisco, Calif. (1969); Bodanszky et al., *Peptide Synthesis*, John Wiley & Sons, Second Edition (1976); Meienhofer, *Hormonal Proteins and Peptides*, 2:46, Academic Press, New York, N.Y. (1983); Merrifield, (1969) *Adv. Enzymol.* 32:221-96; Fields et al., (1990) *Int. J. Peptide Protein Res.* 35:161-214; and U.S. Pat. No. 4,244,946 for solid phase peptide synthesis, and Schroder et al., *The Peptides, Vol.* 1, Academic Press, New York, N.Y., (1965) for classical solution synthesis, each of which is incorporated herein by reference. Appropriate protective groups usable in such synthesis are described in the above texts and in McOmie, *Protective Groups in Organic Chemistry*, Plenum Press, New York, N.Y., (1973), which is incorporated herein by reference.

In general, the solid-phase synthesis methods provided comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

Any peptide of the presently disclosed subject matter can be used in the form of a pharmaceutically acceptable salt. Suitable acids which are capable of the peptides with the provided peptides include inorganic acids, such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the provided peptides include inorganic bases, such as sodium hydroxide, ammonium hydroxide, potassium hydroxide and the like; and organic bases, such as mono-di- and tri-alkyl and aryl amines (e.g., triethylamine, diisopropyl amine, methyl amine, dimethyl amine and the like), and optionally substituted ethanolamines (e.g., ethanolamine, diethanolamine, and the like).

In addition to polypeptide prouroguanylin analogs and/or prouroguanylin fragment analogs, nonpeptide analogs also can be used in the presently disclosed subject matter. These nonpeptide analogs can include any small molecule that shows an activity equivalent to prouroguanylin and/or prouroguanylin fragments. Such analogs can be generated, for example, by combinatorial chemical techniques that optimize their prouroguanylin-like activity.

Examples of diseases that can be treated by molecules of the presently disclosed subject matter include, but are not limited to, kidney disease or dysfunction, including chronic glomerular nephritis, and chronic renal failure, heart disease or heart failure, including edema caused by congestive heart disease, liver disease, including cirrhosis of the liver, and combinations thereof. Molecules of the presently disclosed subject matter also can have use in the control of hypertension.

IV. Therapeutic Methods

The presently disclosed subject matter pertains, in part, to the discovery that infusion of proUGn elicits larger diuretic and natriuretic responses in rats than does infusion of $UGn_{18}$. ProUGn, or molecules derived from it (but distinct from $UGn_{18}$ in rats, and as $UGn_{16}$ in humans), plays a role in these enhanced responses. The presently disclosed subject matter demonstrates that infusing exogenous proUGn into the bloodstream of a subject results in up to a 50-fold increase in urine production. Infusion of proUGn stimulates the kidney to excrete both salt (natriuresis) and fluid (diuresis). Infusion of proUGn can therefore be used in the treatment of diseases that are characterized by salt and fluid retention.

Thus, in some embodiments, the presently disclosed subject matter provides a method of treatment for patients afflicted with diseases that lead to derangements of salt and/or fluid homeostasis, including salt and fluid retention, i.e., are "characterized by salt and fluid retention." Accordingly, the presently disclosed subject matter provides a method of treatment for patients afflicted with kidney disease or dysfunction, including chronic glomerular nephritis, and chronic renal failure, heart disease or heart failure, including edema caused by congestive heart disease, liver disease, including cirrhosis of the liver, and/or hypertension, as well as patients who would benefit from a diuretic drug but are not responsive to conventional diuretics.

A variety of diuretic agents currently are used in clinical practice. Many patients, however, are resistant to the known spectrum of diuretics. While it is not desired to be bound by any particular theory, it is suggested that proUGn works by a mechanism that is distinct from the mechanisms employed by other diuretics. Specifically, the response to proUGn has an unusually slow onset (20 to 40 min after beginning infusion) and an unusually long duration (lasting more than several hours after terminating the infusion). These unusual characteristics place proUGn in a unique category with regard to the known diuretics. Thus, because proUGn appears to work via a novel mechanism, it is of benefit to patients who are resistant to conventional diuretics.

IV.A. Subjects

In some embodiments, the methods of the presently disclosed subject matter can be useful for treatment of a subject, as defined herein. The subject treated in the presently disclosed subject matter in its many embodiments is a human subject, although it is to be understood that the principles of the presently disclosed subject matter indicate that the presently disclosed subject matter is effective with respect to all vertebrate species, including mammals, which are intended to be included in the term "subject". In this context, a mammal is understood to include any mammalian species in which treatment is desirable, particularly agricultural and domestic mammalian species.

Accordingly, the term "subject" as used herein, refers to any invertebrate or vertebrate species. The methods of the presently disclosed subject matter are particularly useful in the treatment of warm-blooded vertebrates. Thus, the presently disclosed subject matter concerns mammals and birds. More particularly, provided is the treatment and/or diagnosis of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they also are of economical importance to humans. Thus, provided is the treatment of livestock, including, but not limited to, domesticated swine (pigs and hogs), ruminants, horses, poultry, and the like.

IV.B. Formulations

A therapeutic composition (e.g., a composition comprising prouroguanylin, a renal metabolite of prouroguanylin, an analog or fragment of prouroguanylin or one of its renal metabolites, or a combination thereof) preferably comprises a composition that includes a pharmaceutically acceptable carrier. Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In some embodiments, the therapeutic composition can contain an additional therapeutic agent in combination with the prouroguanylin, prouroguanylin metabolite, fragment or analog wherein the additional therapeutic agent has diuretic and/or natriuretic properties. The additional therapeutic agent can be administered in the same or a different composition.

Thus, the term "in combination" can refer to the administration of active agents in a single composition or in one or more separate compositions. Common classes of diuretics that would be familiar to one of ordinary skill in the art include carbonic anhydrase inhibitors, thiazide and thiazide-like diuretics, loop (or high-ceiling) diuretics, and potassium-sparing diuretics. Specific examples of such diuretics include, but are not limited to, furosemide, bumetadine, torsemide, hydrochlorothiazide, triamterine, indapamide, ethocrinic acid, spironolactone, and metolazone.

The compositions used in the presently disclosed methods can take such forms as suspensions, solutions or emulsions in oily or aqueous vehicles, and can contain formulatory agents, such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients, such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a therapeutic composition can be formulated in combination with hydrochlorothiazide, and as a pH stabilized core having an enteric or delayed release coating which protects the composition until it reaches the colon.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds also can be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds also can be formulated in rectal compositions (e.g., suppositories or retention enemas containing conventional suppository bases, such as cocoa butter or other glycerides), creams or lotions, or transdermal patches.

IV.C. Doses

The term "effective amount" is used herein to refer to an amount of the therapeutic composition (e.g., a composition comprising prouroguanylin, a renal metabolite of prouroguanylin, an analog or fragment of prouroguanylin or one of its renal metabolites, or a combination thereof) sufficient to produce a measurable biological response (e.g., diuresis and/or natriuresis). Actual dosage levels of active ingredients in a therapeutic composition of the presently disclosed subject matter can be varied so as to administer an amount of the active compound(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich et al., (1966) *Cancer Chemother Rep.* 50:219-244). Drug doses also can be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich et al. (Freireich et al., (1966) *Cancer Chemother Rep.* 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

For additional guidance regarding formulation and dose, see U.S. Pat. Nos. 5,326,902; 5,234,933; PCT International Publication No. WO 93/25521; Berkow et al., (1997) *The Merck Manual of Medical Information*, Home ed. Merck Research Laboratories, Whitehouse Station, N.J.; Goodman et al., (1996) *Goodman & Gilman's the Pharmacological Basis of Therapeutics*, 9th ed. McGraw-Hill Health Professions Division, New York; Ebadi, (1998) *CRC Desk Reference of Clinical Pharmacology*. CRC Press, Boca Raton, Fla.; Katzung, (2001) *Basic & Clinical Pharmacology*, 8th ed. Lange Medical Books/McGraw-Hill Medical Pub. Division, New York; Remington et al., (1975) *Remington's Pharmaceutical Sciences*, 15th ed. Mack Pub. Co., Easton, Pa.; and Speight et al., (1997) *Avery's Drug Treatment: A Guide to the Properties, Choice, Therapeutic Use and Economic Value of Drugs in Disease Management*, 4th ed. Adis International, Auckland/Philadelphia; Duch et al., (1998) *Toxicol. Lett.* 100-101:255-263.

IV.D. Routes of Administration

Suitable methods for administering to a subject a composition of the presently disclosed subject matter include, but are not limited to, systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

The particular mode of drug administration used in accordance with the methods of the presently disclosed subject matter depends on various factors, including but not limited to the therapeutic agent and/or drug carrier employed, the severity of the condition to be treated, and mechanisms for metabolism or removal of the drug following administration.

V. Diagnosis and Monitoring of Diseases Related to Fluid and/or Sodium Homeostasis The presently disclosed subject matter also demonstrates that the levels of endogenous proUGn in the plasma vary with oral salt intake: increased oral salt leads to increased circulating proUGn, whereas decreased oral salt leads to decreased circulating proUGn. Therefore, the measurement of plasma proUGn (and/or the ratio of plasma proUGn to plasma $UGn_{18}$ in rats, and as $UGn_{16}$ in humans) can serve as a diagnostic tool for evaluating the onset and progression of diseases involving the kidney, the heart, the liver, the intestine, and the circulatory system. Thus, in some embodiments, the presently disclosed subject matter provides a method of diagnosing and/or monitoring a disease involving fluid and/or sodium homeostasis. Representative disease states include, but are not limited to, diseases that lead to volume expansion, decreased renal function, decreased cardiac function, and/or high blood pressure, all of which elevate the levels of proUGn in the plasma.

In some embodiments, the present methods involve the quantitative analysis of prouroguanylin in a biological sample through the use of an anti-proUGn specific immunoassay.

Uroguanylin radioimmunoassays (RIAs) currently available in the art are unsuitable for measuring proUGn, as they make use of a $UGn_{18}$-based standard curve to calculate peptide levels, and none have established the relative affinities of the antibody for proUGn and $UGn_{18}$. The presently disclosed subject matter provides an immunoassay tailored for accurate, quantitative detection of proUGn, avoiding complications that arise from simultaneous detection of the propeptide and its best-known cleavage product, $UGn_{18}$. Thus, the presently disclosed subject matter also provides in some embodiments an immunoassay procedure to measure plasma levels of proUGn.

General techniques for preparing tissue and plasma samples for use in immunoassays, as well as standard protocols for running the immunoassays will be known to one of skill in the art.

In some embodiments, the anti-proUGn antibodies provided by the presently disclosed subject matter for use in detecting biological levels of proUGn are polyclonal antibodies. The phrase "polyclonal antibody" in its various grammatical forms refers to a population of antibody molecules that contain many species of antibody combining site. A portion of the population of the polyclonal antibodies will display a binding affinity for a particular epitope of interest. In the presently disclosed subject matter, the immunogen of interest is a portion of the prouroguanylin peptide distinct from the amino acid sequence of $UGn_{18}$ in rats, and as $UGn_{16}$ in humans. Thus, for example, one of the anti-proUGn polyclonal antibodies (6910) described herein was elicited against an antigen made using an immunogen containing the amino acid sequence PALPLDLQPVCASQE (SEQ ID NO: 7).

As used herein, the term "antigen" refers to a molecule that binds to an antibody or a T cell receptor. Antigens that bind to antibodies include all classes of molecules. As used herein, the term "epitope" refers to the specific portion of a macromolecular antigen to which an antibody binds. In the case of a protein antigen recognized by a T cell, an epitope is the peptide portion that binds to an MHC molecule for recognition by the T cell receptor. Polyclonal antibodies represent the entire immune response to an antigen and will therefore contain antibodies that bind to epitopes other than the epitope of interest.

As used herein the term "immunogen" refers to an antigen that induces an immune response.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts.

Methods of the presently disclosed subject matter would be amenable to the use of monoclonal antibodies produced from the epitopes described herein for anti-proUGn antibodies. A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler & Milstein, (1975) *Nature* 256:495-497, which description is incorporated by reference. Additional methods are described by Zola, *Monoclonal Antibodies: a Manual of Techniques*, CRC Press, Inc, Boca Raton, Fla. (1987). The hybridoma supernates so prepared can be screened for the presence of antibody molecules that immunoreact with prouroguanylin or fragments or analogs thereof.

Briefly, to form the hybridoma from which the monoclonal antibody composition is produced, a myeloma or other self-perpetuating cell line is fused with lymphocytes obtained from the spleen of a mammal hyperimmunized with antigen comprising a proUGn epitope. It is preferred that the myeloma cell line used to prepare a hybridoma be from the same species as the lymphocytes. Typically, a mouse of the strain 129 GlX+ is a preferred mammal. Suitable mouse myelomas for use in the presently disclosed subject matter include the hypoxanthine-aminopterin-thymidine-sensitive (HAT) cell lines P3X63-Ag8.653, and Sp2/0-Ag14 that are available from American Type Culture Collection (ATCC), Manassas; Va., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of the presently disclosed subject matter can be identified using an enzyme-linked immunosorbent assay (ELISA).

A provided monoclonal antibody also can be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules can then be further isolated by employing techniques known to those of ordinary skill in the art. Media useful for the preparation of these compositions are both well known in the art and commercially available and include synthetic culture media, inbred mice and the like. An exemplary synthetic medium is Dulbecco's minimal essential medium (DMEM) Dulbecco et al., (1959) *Virol.* 8:396) supplemented with 4.5 gm/1 gm glucose, 20 mM glutamine, and 20% fetal calf serum. An exemplary inbred mouse strain is the Balb/C.

Other methods of producing a monoclonal antibody, a hybridoma cell, or a hybridoma cell culture also are well known. See, for example, the method of isolating monoclonal antibodies from an immunological repertoire as described by Sastry et al., (1989) *Proc. Natl. Acad. Sci. U.S.A.* 86:5728-5732; and Huse et al., (1989) *Science* 246:1275-1281.

It also is possible to determine, without undue experimentation, if a monoclonal or polyclonal antibody has the same (i.e., equivalent) specificity (immunoreaction characteristics) as an antibody of the presently disclosed subject matter by ascertaining whether the former prevents the latter from binding to a preselected target molecule. If the antibody being tested competes with the antibody of the presently disclosed subject matter, as shown by a decrease in binding by the antibody of the presently disclosed subject matter in standard competition assays for binding to the target molecule when present in the solid phase, then it is likely that the two antibodies bind to the same, or a closely related, epitope.

Still another way to determine whether an antibody has the specificity of an antibody of the presently disclosed subject matter is to pre-incubate the antibody of the presently disclosed subject matter with the target molecule with which it is normally reactive, and then add the antibody being tested to determine if the antibody being tested is inhibited in its ability to bind the target molecule. If the antibody being tested is inhibited then, in all likelihood, it has the same, or functionally equivalent, epitopic specificity as the monoclonal antibody of the presently disclosed subject matter.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods for Examples 1-7

The cDNA sequence of rat prouroguanylin, along with suitable methods for tissue and extract preparation, and Northern and Western blotting techniques have been previously described. See Li, Z. et al., *Regul. Pept.*, 68, 45-56 (1997). Rat proGn has been previously cloned. See Currie, M. G., et al., *Proc. Natl. Acad. Sci.*, 89, 947-951 (1992).

The sequence for rat prouroguanylin is:

(SEQ ID No. 8)
VYIKYHGFQVQLESVKKLNELEEKQMSDPQQQKSGLLPDVCYNPALPLDL

QPVCASQEAASTFKALRTIATDECELCINVACTGC.

The sequence for rat proguanylin is:

(SEQ ID No. 9)
MNAWLLSVLCLLGALAVLVEGVTVQDGDLSFPLESVKQLKHLREVQEPTL

MSHKKFALRLPKPVAPELCSQSAFPEALRPLCEKPNAEEILQRLEAIAQD

PNTCEICAYAAGTGC.

Experiments were performed with 200-250 g male Sprague Dawley rats (Charles River Laboratories, Wilmington, Mass., United States of America). Rat test diets were obtained from a commercial supplier (Harlan Teklad, Madison, Wis., United States of America). For some experiments, anephric animals were prepared by surgical acute ligation of the renal pedicles. As necessary, animals were anesthetized with Nembutal (60 mg/kg body weight ip).

Radioactive proUGn was prepared by coupled in vitro transcription/translation in the presence of $^{35}$S-Cys and $^{35}$S-Met from a cDNA template that encoded full-length proUGn (minus the signal peptide).

In general, biological samples were fractionated by SDS-PAGE prior to performing immunoassays to ensure that all molecular species detected had a molecular weight corresponding to full-length proUGn, thus eliminating any antibody cross-reactivity with proUGn cleavage products or other irrelevant proteins that could react non-specifically with the antibodies.

Unless otherwise stated, HPLC conditions for the detection and identification of proUGn and related peptides are as follows: Vydac 218TP™ C-18 reverse-phase column (Grace Vydac, Hesperica, Calif., United States of America); equilibration of the column with $H_2O$ with 0.1% TFA for 25 minutes, followed by a 30 minutes gradient from 0% acetonitrile (with 0.1% TFA) to 50% acetonitrile (with 0.1% TFA), 5 min wash with 100% acetonitrile (0.1% TFA).

Na, K, and fluid excretion: Na and K concentrations are analyzed on an IF model 943 flame photometer (Instrumentation Laboratory Company, Lexington, Mass., United States of America). Urine is collected from ureteric canulae or by the use of metabolic cages. Urine volume is determined gravimetrically.

Protease inhibitor, when used, is a commercial mixture of inhibitors from Sigma (Sigma-Aldrich, Milwaukee, Wis., United States of America) containing 1 mM EDTA, 0.01% bacitracin, 2.5 mM 4-(2-aminoethyl)-benzenesulfonyl fluoride, 38 µM pepstatin A, 35 µM trans-epoxysuccinyl-L-leucylamido(4-guanidino)butane, 0.1 mM bestatin, 55 µM leupeptin, and 2 µM aprotinin.

Example 1

Anti-proUGn and Anti-proGn Antibodies

Antibodies were raised against two different 15 amino acid regions of rat proUGn molecule as described previously. See Perkins, A., et al., *Gastroenterology*, 113, 1007-1014 (1997). Antibodies against two regions of rat proGn also were produced. The sequences used as antigens for the two anti-proUGn antibodies, 6910 and 6912, and the two anti-proGn antibodies, 2538 and 6240, are shown in FIG. 1.

The amino acid sequence for the immunogen used to raise the polyclonal anti-proUGn antibody 6910 is PALPLDLQPVCASQE (SEQ ID NO: 7).

The amino acid sequence for the immunogen used to raise the polyclonal anti-proUGn antibody 6912 is QQQKSGLLPDVCYN (SEQ ID NO: 10)

The amino acid sequence for the immunogen used to raise the polyclonal anti-proGn antibody 2538 is VQDGDLSFPLESVK (SEQ ID NO: 11).

The amino acid sequence for the immunogen used to raise the polyclonal anti-proGn antibody 6240 is LCEKPNAEEILQRLE (SEQ ID NO: 12).

Figure 3:
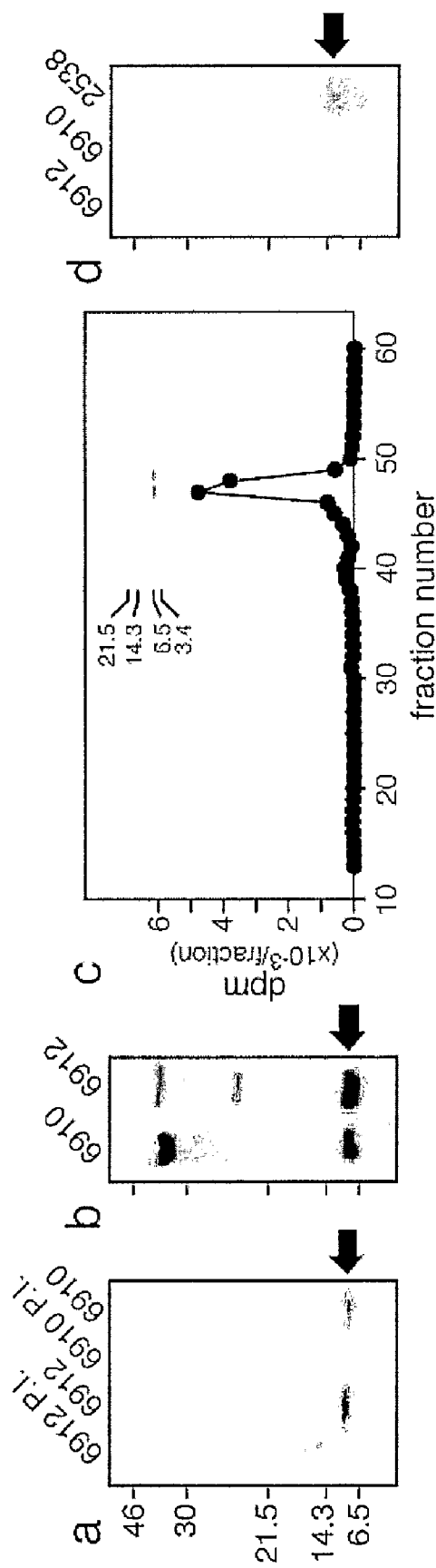
FIGS. 3a-3d show the characterization and validation of the anti-proUGn antibodies 6910 and 6912.

FIGS. 3a-3d show the characterization and validation of the anti-proUGn antibodies 6910 and 6912. FIG. 3a is an autoradiogram of an SDS PAGE gel showing that antibodies 6910 and 6912 immunoprecipitate radiolabeled proUGn. Antibodies in serum removed from the rabbits prior to immunization (used in the lanes marked 6912 P.I. and 6910 P.I.) do not immunoprecipitate the propeptide, suggesting that the immunoreactivity is the result of immunization with anti-proUGn antigens and not a non-specific reaction as the result of antibodies already present in the rabbit serum. As indicated by the tick marks on the left side of the blot, the immunoprecipitated protein has a molecular weight of approximately 8.5 kDa, the correct size for full-length proUGn after removal of the signal peptide. Thus the reaction preparing radiolabeled proUGn also appeared to give the desired product. FIG. 3b shows a Western blot of the protein detected by the anti-proUGn antibodies from tissue samples of rat small intestine. The antibodies label a protein, presumably native proUGn, that appears to be the same size as the 8.5 kDa radiolabeled proUGn precipitated in FIG. 3a. The antibodies also both label higher-molecular weight proteins, but in this case the crossreacting molecules recognized by one antibody do not appear to be equivalent to those recognized by the other (thus indicating that they are non-specifically immunoreactive molecules that are unrelated to proUGn). Preimmune sera was completely non-reactive. FIG. 3c shows that the radiolabeled proUGn used in the experiment that produced FIG. 3a has the same HPLC retention time as the immunoreactive 8.5-kDa protein from the rat small intestine. The solid symbols on the HPLC chromatogram are the scintillation counting results of the fractions collected from chromatography of the radiolabeled proUGn. The inset Western blot shows the 8.5 kDa protein present in the fractions collected at the corresponding timepoints in the HPLC of the intestine sample. FIG. 3d is a Western blot showing that the anti-proUGn antibodies (6910 and 6912) do not recognize recombinant proGn (prepared analogously to radiolabeled proUGn). Anti-proGn antibody (lane marked 2538) does interact with radiolabeled proGn.

Figure 4:
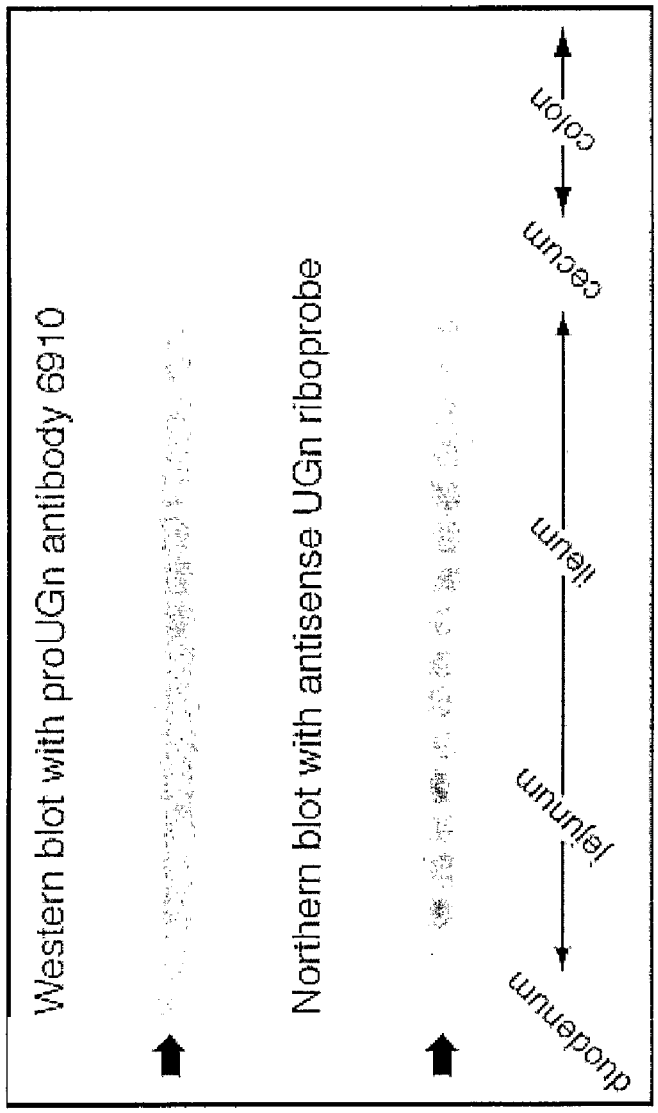
FIG. 4 shows the distribution of proUGn polypeptide (upper Western blot with proUGn antibody 6910, proUGn marked by the arrow) and uroguanylin mRNA (lower Northern blot with antisense UGn riboprobe, uroguanylin transcript marked by the arrow) along the rostrocaudal axis of the intestine.

The anti-proUGn antibodies were also used to determine the propeptide distribution in tissues in different sections of the rat intestine. FIG. 4 compares Western blot data (upper blot) from experiments with anti-proUGn antibody 6910 and Northern blot data (lower blot) from experiments with anti-sense UGn riboprobe. Tissue samples used in the experiments were taken from different sections of rat intestine as indicated below the blots; thus, the blots show the distribution of proUGn peptide and uroguanylin mRNA along the entire rostrocaudal axis. Each blot is representative of multiple determinations, and the results are reproducible from experiment to experiment (n=4 for each technique). The propeptide and the mRNA transcript have essentially indistinguishable regional patterns of expression within the intestine. (FIG. 4 is reproduced from Qian, X., et al., *Endocrinology*, 141, 3210-3224 (2000).

In an initial test to determine if the anti-proUGn and anti-proGn antibodies could detect proUGn and proGn in plasma, five mg of rat plasma protein was fractionated by reverse-phase HPLC. Fractions bracketing the known retention times of proUGn and proGn, as established with authentic standards, were collected. The individual fractions were immunoblotted with anti-proUGn antibody 6910 or anti-proGn antibody 2538.

Figure 5:
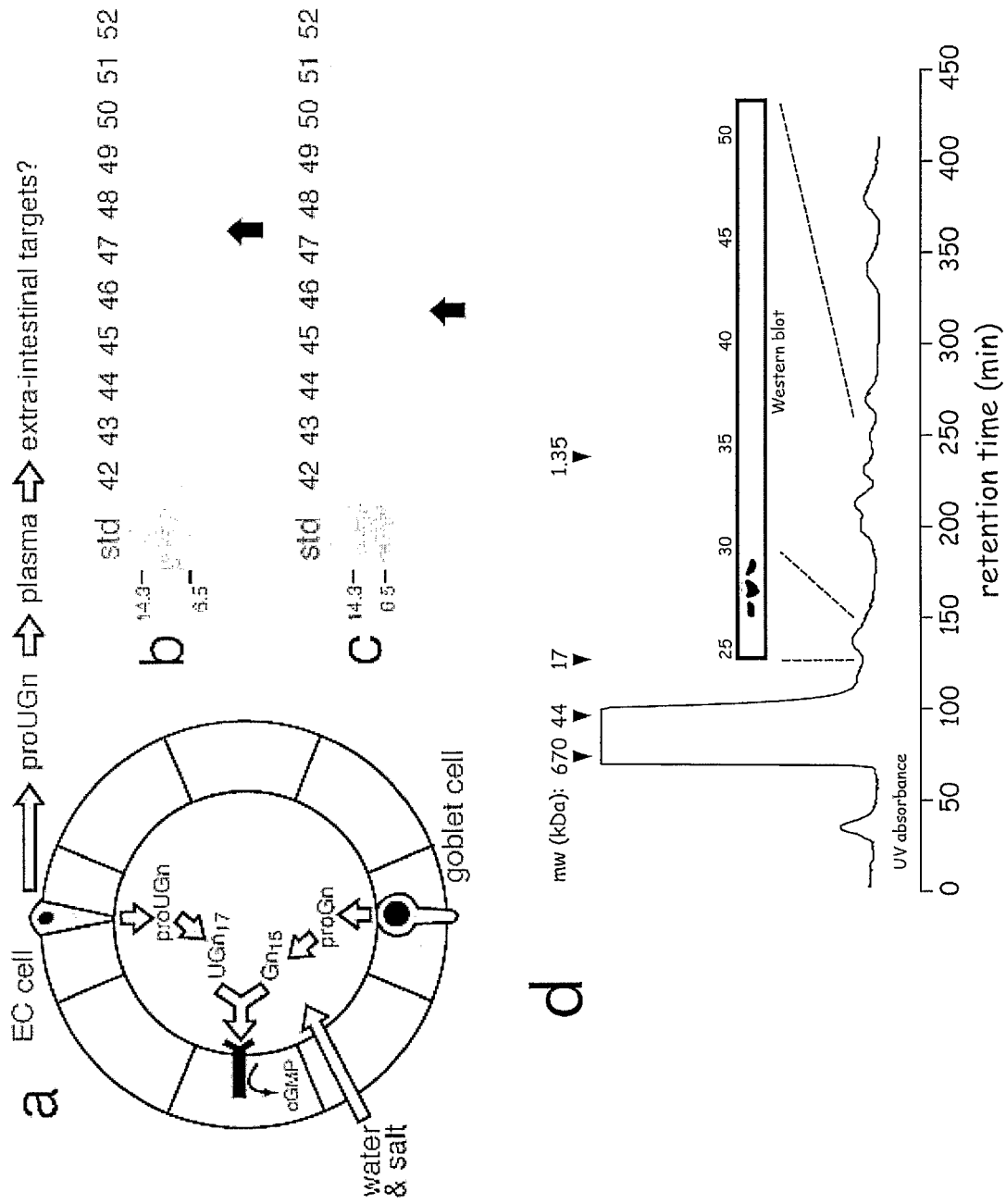
FIGS. 5a-5d show cell secretion and plasma detection of proUGn and proGn.

FIG. 5a shows a schematic of the proposed cell secretion of proUGn and proGn. ProGn is expressed in the goblet cells and secreted apically into the intestinal lumen. In the lumen, proGn is presumably reduced to $Gn_{15}$ by gut proteases to activate luminally-oriented GC-C receptors. In contrast, proUGn is expressed in EC cells and secreted both apically and basolaterally. Thus only proUGn should be detected in the plasma. The results of the plasma immunoblotting experiments appear to agree with this schematic. FIG. 5b shows Western blots using anti-proUGn antibody 6910 with eleven HPLC fractions (42-52) from the HPLC fractionation of the rat plasma. An approximately 8.5 kDa protein is detected in fractions 47 and 48 (as indicated with the arrow). The anti-proGn antibody 2538 does not detect any protein from the HPLC fractions (FIG. 5c). The fractions (455 and 46) that should contain proGn, based on the HPLC retention time of an authentic sample, are marked with an arrow. The lanes marked "std" in FIGS. 5b and 5c were loaded with either authentic proUGn (FIG. 5b) or authentic proGn (FIG. 5c) as a control.

Subsequent improvements of this technique replace the reverse phase column with an HPLC size-exclusion column. This improved procedure gives better separation between proUGn and other abundant plasma proteins, such as albumin and immunoglobulins. Removal of these abundant interfering proteins greatly improves the resolution of the Western blot procedure, and thus greatly increases the sensitivity of the assay (see FIG. 5d).

Example 2

Quantitative ProUGn-Specific Immunoassay

The quantitative immunoassay was performed on a 20-lane gel with the two outermost lanes left blank to avoid edge effects. Six lanes on the left hand side were used to construct a standard curve and were loaded with a dilution series of r-proUGn (500 fmol, 250 fmol, 125 fmol, 62.5 fmol, 31.3 fmol, and 15.6 fmol). Two additional lanes were used for molecular weight standards and an internal calibration standard. The remaining 10 lanes were loaded with experimental samples. The gel contents were co-electrophoresed and co-transferred to a nitrocellulose capture membrane by conventional immunoblot methodology. The membrane was then blocked overnight with 2% teleostean fish gel, incubated with an anti-proUGn primary antibody (6910 or 6912), washed extensively, and incubated with an IRDye™ 800-conjugated goat anti-rabbit secondary antibody (Li-Cor Biosciences, Lincoln, Nebr., United States of America). After additional washing, a Li-Cor Biosciences Odyssey® Infrared Imaging System was used to measure the amount of secondary antibody bound to pro-UGn.

A line was fit to the detected infra-red (IR) intensity readings produced by the standards, and the quantity of unknown r-proUGn was determined by interpolation. The assay was determined to be linear up to at least 8 pmol, with a detection limit slightly higher than the 15.6 fmol standard. The average coefficient of variation for identical test samples run in the same assay was 4.2±0.2%.

Figure 6:
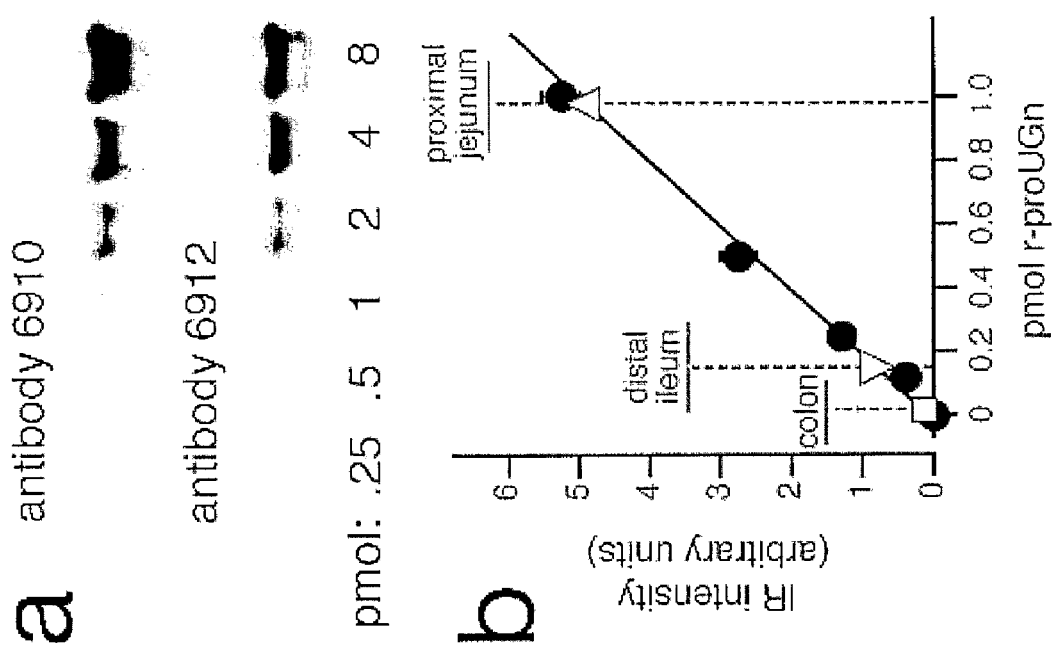
FIGS. 6a and 6b show a quantitative immunoassay for proUGn.

Results from the quantitative immunoassay are shown in FIGS. 6a and 6b. FIG. 6a shows the varying infrared intensity produced by the dilution series of r-proUGn tested with the two different anti-proUGn antibodies (6910 and 6912). The data from these lanes was used to produce the standard curve indicated by the line in FIG. 6b. The amount of proUGn from experimental samples taken from rat colon, rat distal ileum and rat proximal jejunum was determined by fitting the IR intensity data produced from these samples to the standard curve. Thus, as shown in FIG. 6b, colon samples contain almost no proUGn, distal ileum samples contain a little less than 0.2 pmol proUGn per 60 μg of total protein and the sample from the proximal jejunum contains approximately 1.0 pmol proUGn per 60 μg of total protein.

Example 3

Plasma Levels of proUGn in Response to Salt Intake

Acute Model for Orogastric Salt Loading: Before the start of experiments, animals were maintained on a normal salt diet (standard rat chow, 0.5% NaCl). Food, but not water, was withdrawn 12 hr before the acute salt loading experiment. At the start of the experiment, the animal was anesthetized and fitted with a gastric tube coupled to a pressure transducer to deliver test solutions and monitor gastric emptying, along with a PE240 tracheotomy tube to ensure unobstructed ventilation. An indwelling canula in the jugular vein was used for intravenous (iv) infusions, and an arterial pressure transducer was connected to a canula in the carotid artery to monitor blood pressure. Urine was collected from individual ureteric canulae to assess renal function and proUGn excretion. The portal vein was exposed by retracting the intestine and reflecting the liver behind a gauze pad. All animals received a constant maintenance infusion of saline containing 2% BSA through the jugular vein canula (30 μl/min/100 g body weight). Depth of anesthesia, blood pressure, hematocrit, and urine production were monitored as indices for acceptable experimental conditions. Once these parameters stabilized, plasma sampling (150 μl) from the portal vein and the carotid artery was begun, continuing at 60 min intervals, for the duration of each experiment. Sequential 30 min urine samples also were collected over the course of each experiment. At the end of each experiment, the proximal small intestine, proximal colon, kidney, and liver were removed to measure levels of proUGn and uroguanylin mRNA expression.

To determine if baseline plasma and urine proUGn levels were affected by the experimental conditions, a control group of six rats was tested according to the protocol above without receiving an intragastric infusion of salt. A test group of six animals received 3 mL of 300 mM NaCl by gavage at 30 min.

Figure 7:
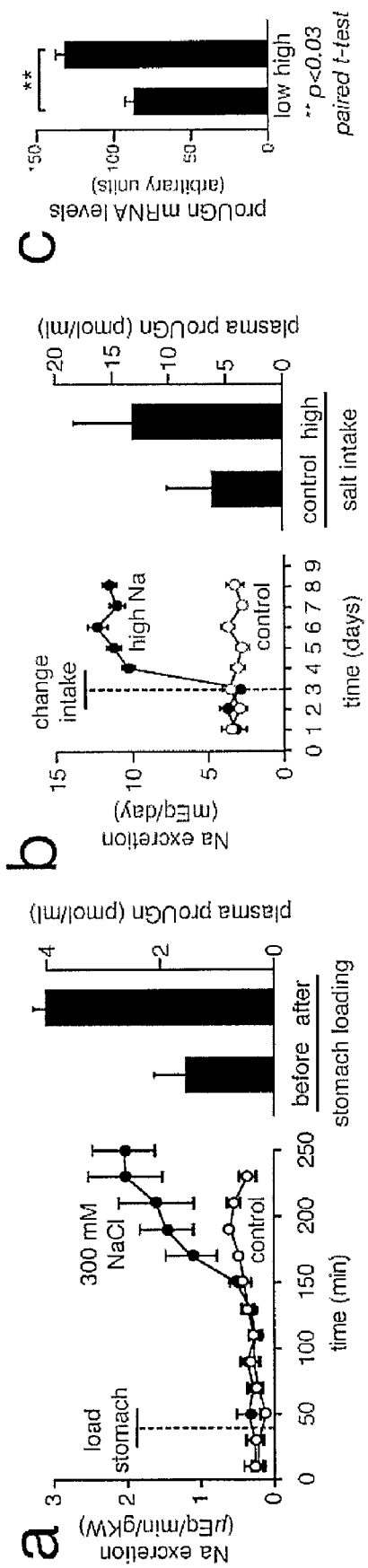
FIGS. 7a-7c show the changes in sodium (Na) excretion, plasma proUGn levels, and intestinal uroguanylin mRNA expression induced by acute and chronic oral salt-loading protocols.

FIG. 7a shows that there is a large increase in urinary Na excretion beginning about 100 minutes after the intragastric salt infusion (solid circles). No real increase in urinary Na output was seen in the control animals (open circles). A corresponding increase in the level of plasma proUGn was seen. The bar graph at the right of FIG. 7a shows that plasma concentrations of proUGn measured 100 minutes after the salt loading ("after" bar in the graph) was more than twice that of proUGn plasma concentrations prior to the salt loading ("before" bar in the graph).

Chronic Model for Orogastric Salt Loading: Animals were maintained in individual metabolic cages for three days on standard rat chow, then placed on either standard chow (0.5% NaCl) or high Na chow (2% NaCl) for four days (n=6 per treatment group). The diets had different salt concentrations, but were identical in all other respects (protein, lipid, carbohydrate, and fiber content). Food and water consumption (available ad libitum) were monitored daily. The initial three-day period provided control (pre-stimulus) data for each animal. Plasma and urine samples were collected twice per day during the first 3 days, corresponding to lights on (6 am) and lights off (6 pm); at 3 hr intervals during the first 24 hr after switching diets; and twice per day for the remainder of the study. Plasma samples (100 μL) were withdrawn via an indwelling catheter placed in a carotid artery. Urine was collected continuously into chilled tubes preloaded with a protease inhibitor cocktail (Sigma, Milwaukee, Wis., United States of America). ProUGn levels were determined in plasma and urine by immunoassay, and urinary Na and K excretion were measured by flame photometry. At the end of the experiment, tissues were removed (the proximal 10 cm of jejunum, the proximal 10 cm of colon, the kidney and the liver), and uroguanylin mRNA levels were determined by Northern blotting. Levels of uroguanylin mRNA measured by Northern blotting were normalized to β-actin mRNA levels.

Results from the chronic salt loading experiments are shown in FIGS. 7b and 7c. FIG. 7b shows that urinary sodium excretion dramatically increases after the dietary salt change at day 3. Data from animals with the high salt diet are shown in the solid circles, data from the control group are shown in the open circles. As with acute changes in salt intake, chronic changes in dietary salt intake also caused an increase in plasma proUGn levels. The bar graph at the right of FIG. 7b shows that the animals on the high salt diet had plasma proUGn concentrations at about 13 pmol/mL compared to the 5-6 pmol/mL concentrations seen in the control animal plasma. FIG. 7c shows that Jejunal uroguanylin mRNA expression in animals maintained for 6 days on a high salt diet was greater than that of the animals maintained on a low salt diet for 6 days.

Example 4

Kidney Clearance of Plasma ProUGn

Figure 8:
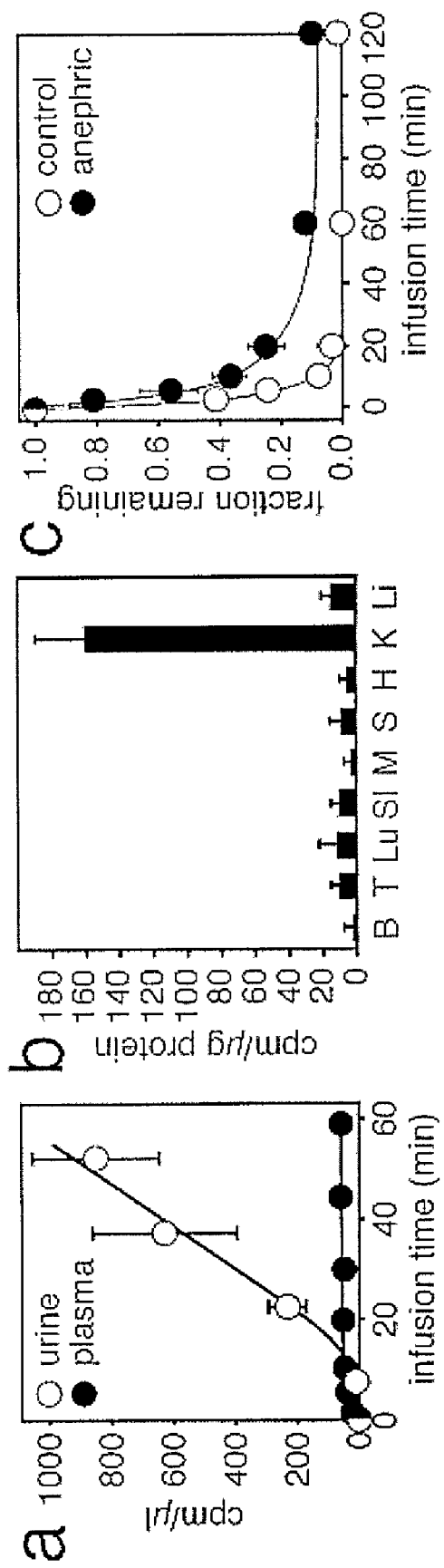
FIG. 8a-8c show the fate of infused proUGn in normal and anephric rats.

A solution containing radioactively-labeled r-proUGn was infused by iv into anesthetized rats for 60 min. The concentration of radioactivity in the plasma and the urine was measured via scintillation counting at timepoints throughout the infusion. FIG. 8a shows that while plasma levels (solid circles) of proUGn remained steady, urine levels (open circles) increased dramatically over the time course of the infusion. At the end of the 60 min infusion, tissue samples were collected from the brain, thymus, lung, small intestine, skeletal muscle, spleen, heart, kidney, and liver and assayed for radioactivity by scintillation counting. As shown in FIG. 8b, only the kidney samples contained significant levels of radioactivity corresponding to the presence of $^{35}$S-proUGn.

To measure the rate of kidney clearance of proUGn, plasma levels of $^{35}$S-proUGn were monitored following bolus injection of the radiolabelled propeptide. Bolus injections (about $10^6$ cpm) were given to groups of control (i.e., normal) rats and to anephric rats. At various timepoints after the injection, blood samples were removed and fractionated by HPLC. Radioactivity in each HPLC fraction was measured in a scintillation counter. FIG. 8c shows that the proUGn was cleared more quickly in the control animals (open circles) than in the anephric animals (solid circles). Taken together, the results from these experiments indicate that the kidney appears to be the major route of clearance for proUGn.

Example 5

Plasma and Kidney ProUGn Metabolism

Plasma samples were taken 2, 5, and 10 min after bolus injection of $^{35}$S-proUGn (about $10^6$ cpm) into the carotid artery (n=2 for each timepoint). Urine was collected for 30 min at the end of a 60 min arterial infusion of $^{35}$S-proUGn (n=7). The cpm/μL in the infused material was approximately 100 times lower than the cpm/μL in the solution used for the bolus injection. Plasma and urine samples were applied to the HPLC column and eluted, with the radioactivity in each fraction measured in a scintillation counter.

Figure 9:
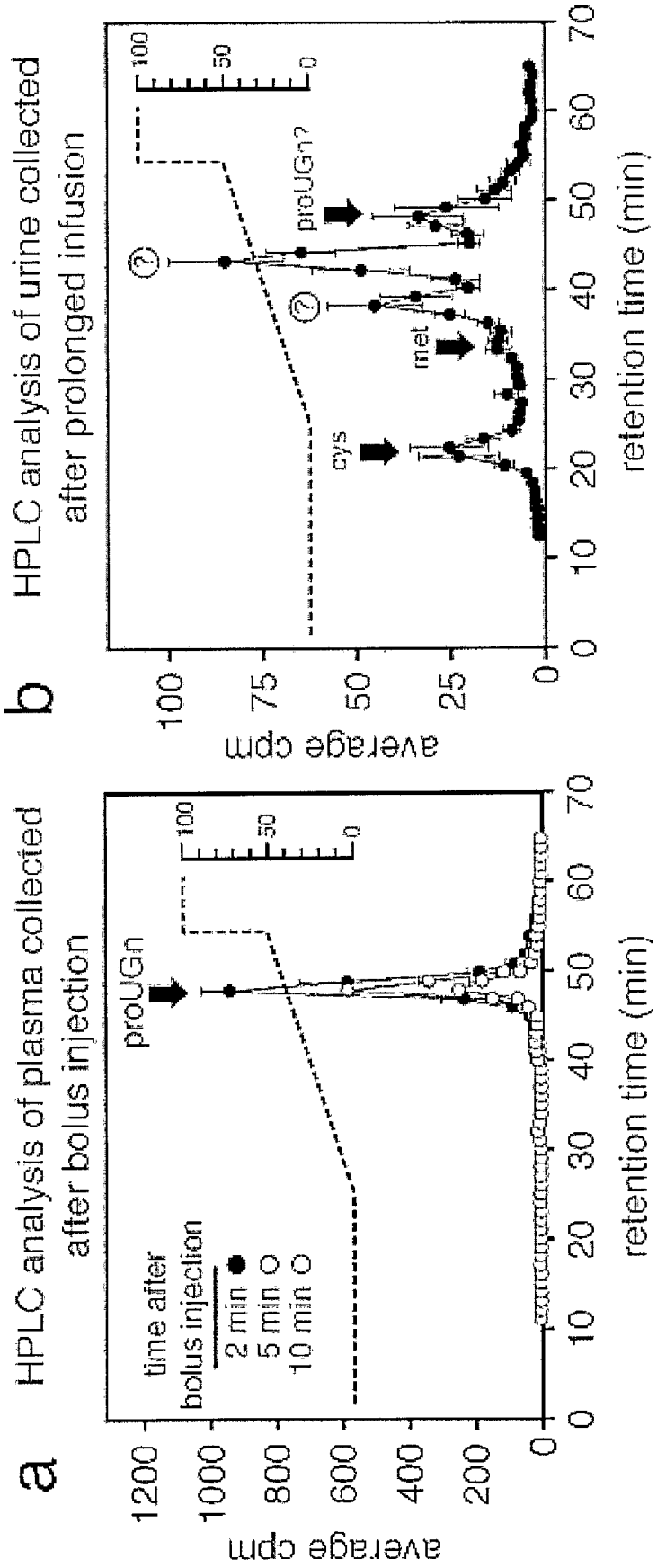
FIGS. 9a and 9b show the HPLC analysis of proUGn metabolites in plasma and urine.

As further evidence that the kidney is essential for proUGn clearance and as a possible indication that the kidney is a site of action for proUGn or a non-UGn$_{18}$ proUGn metabolite, the HPLC analysis of injected $^{35}$S-proUGn revealed that the proUGn appears to remain intact in plasma (FIG. 9a). Although the concentration decreased with time, no new radiolabelled products appeared. Conversely, HPLC analysis of radioactive species in the urine after prolonged infusion of $^{35}$S-proUGn reveals at least two, and possibly three, proUGn-related products (FIG. 9b). The peak at 43 minutes has a retention time similar to proUGn; and, therefore, structural studies similar to those proposed in Example 9 below, are necessary to unambiguously determine if the peak is related to a new proUGn fragment or is intact proUGn, itself. Peaks correlating to free radiolabelled cysteine and methionine also were detected.

Example 6

Diuresis and Natriuresis Induced by Infused ProUGn

Figure 10:
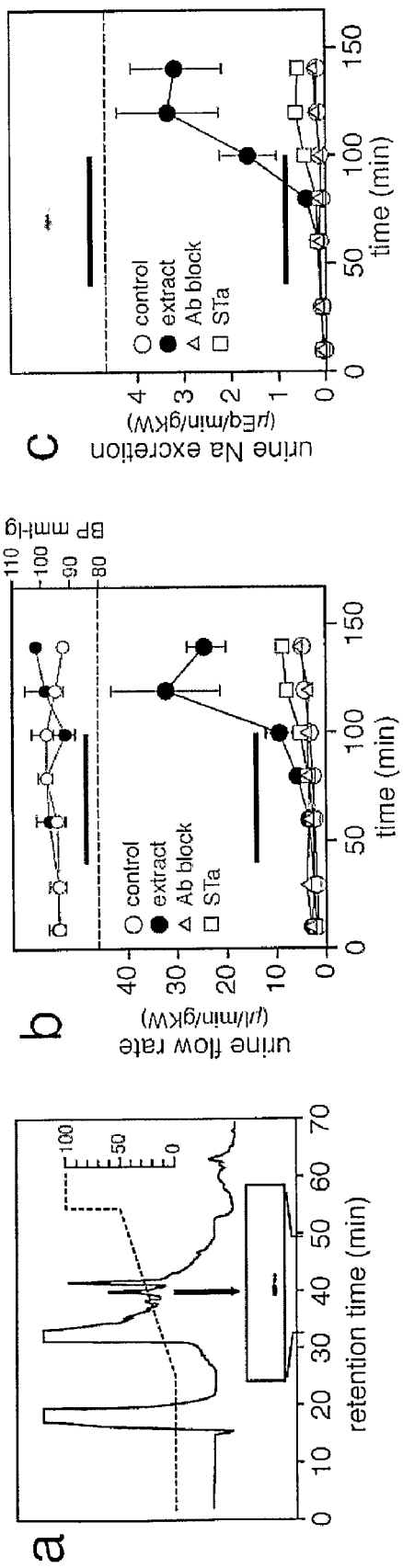
FIGS. 10a-10c show the purification of native proUGn and the biological effects of infused native proUGn on urine flow, salt excretion and blood pressure.

Native proUGn is purified from rat small intestine. Animals are sacrificed by anesthetic overdose, and approximately 20 cm of proximal small intestine is removed. The tissue is cut longitudinally, rinsed with saline, and the mucosal layer is isolated by scraping with a microscope slide. Scraped material is snap-frozen on a metal plate chilled to −78.5° C., then homogenized in 50 mM HEPES, pH 7.4, containing protease inhibitor. The homogenate is cleared by centrifugation at 50,000×g, and the supernate is fractionated sequentially by HPLC on a MonoQ anion exchange column and a VYDAC C-18 reverse-phase column. The HPLC chromatogram of this second chromatography step is shown in FIG. 10a, with a Western blot of the individual HPLC fractions shown in the inset, confirming the presence of proUGn. The purified material was dried to remove the HPLC solvents and resuspended in physiological saline. Recovery is measured by quantitative proUGn immunoassay.

Native proUGn is infused for 60 min into a group of 5 anesthetized rats, the standard infusion containing approximately 180-pmol peptide. Given an estimated rat plasma volume of 10 mL, the infusion rate was approximately 3 pmol/mL/min. Blood pressure, urine production, and sodium excretion were monitored for approximately 40 minutes prior to the infusion, during the infusion, and for approximately 50 minutes after the infusion to measure the effect of the proUGn on diuresis and natriuresis. For comparison, a control group of five rats was infused with regular saline, one rat was infused with a solution of proUGn that had been neutralized by incubation with antibodies 6910 and 6912, and one rat was infused with a solution containing STa at 5 µg/kg/hr.

FIG. 10b shows an increase in urine flow in rats infused with extracted proUGn (solid circles). The time corresponding to the infusion is indicated by the solid horizontal bar in the figure. The increase in urine flow started during the course of the infusion, but continued after the infusion was complete. No increase in urine flow was seen in the control animals (open circles), the animals that received immuno-neutralized proUGn (triangles) or the animals receiving STa (squares). As shown in FIG. 10c, sodium excretion mirrored the increase in urine flow rate. The Western blot inset in FIG. 10c shows urinary proUGn excretion detected during the infusion. Each sample in the Western blots shown above the dotted line in FIG. 10c represents 50% of the total urine collected over a 20-minute period before, during, and after peptide infusion from a representative animal.

The results from this experiment indicate that infused proUGn has potentially stronger diuretic and natriuretic effects than $UGn_{18}$. Sodium excretion increased from 60 nmol/min to 3200 nmol/min following proUGn infusion. This response is many times greater than the responses reported in the literature for animals infused with $UGn_{18}$. See Fonteles, M. C., et al., *Am. J. Physiol.*, 275, F191-F197 (1998); Carrithers, S. L., et al., *Braz. J. Med. Biol. Res.*, 32, 1337-1344 (1999); Carrithers, S. L., et al., *Kidney Int.*, 65, 40-53 (2004). That diuresis and natriuresis were abolished by preabsorbing the infusate with a mixture of antibodies 6910 and 6912, indicates that the biological activity is genuinely associated with proUGn, rather than a co-eluting impurity obtained during the extraction of proUGn from intestinal tissue.

Example 7

Figure 11:
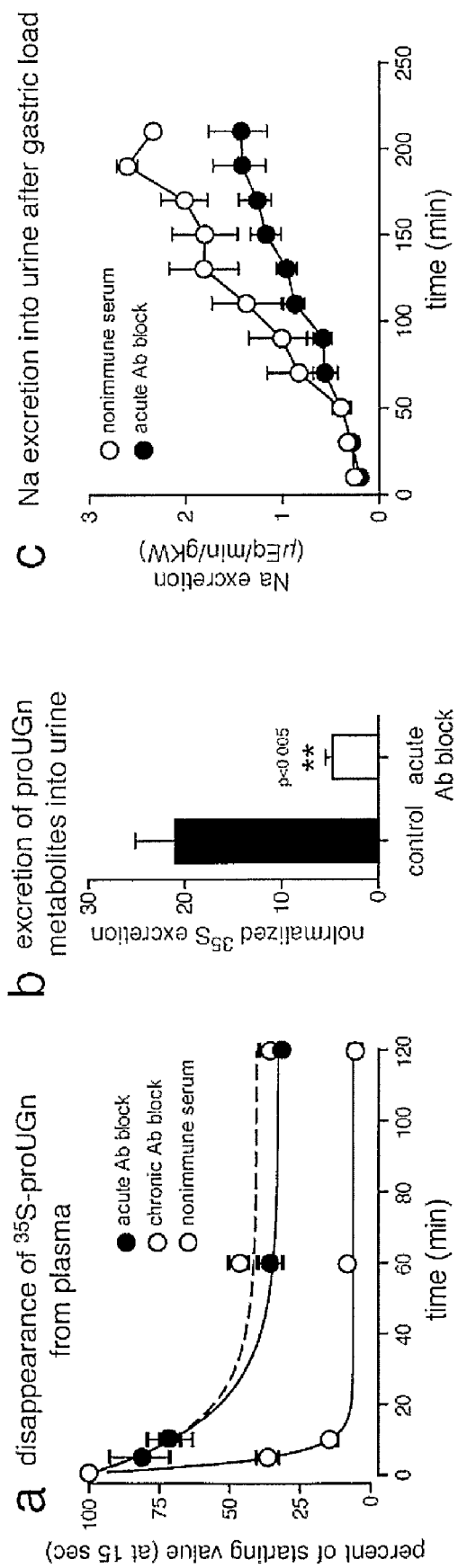
FIGS. 11a-11c show the effects of exogenously-infused circulating anti-proUGn antibodies.

Effects of Circulating anti-proUGn Antibodies on the Production of proUGn Metabolites and Sodium Excretion After an Acute Oral Salt Load Animals treated with the standard bolus injection of $^{35}$S-proUGn also were given a prior iv injection of 1 mL of rabbit anti-proUGn antibodies (500 µL each of 6910 and 6912). Control animals given the bolus injection of $^{35}$S-proUGN received a prior 1 mL injection of non-immunogenic rabbit serum. Plasma samples were taken at various timepoints over the next two hours and analyzed via scintillation counting for the disappearance of $^{35}$S compared to the starting value. Urine was collected throughout the experiment and analyzed for excretion of radioactive material. As shown in FIG. 11a, immune-blocking with the anti-proUGn antibodies led to a pronounced retardation of $^{35}$S-proUGn clearance from the plasma. The bar graph in FIG. 11b shows that the immune blocking also reduces excretion of proUGn metabolites in the urine compared to control.

In a follow-up experiment, groups of control animals and groups of animals receiving anti-proUGn antibodies also were given 3 mL of 300 mM NaCl via gavage as in Example 3. Urine samples were collected and quantified for Na. As shown in FIG. 11c, the rate of development of the natriuretic response following gastric loading was decreased from 13±1 nEq/min² in control rats (open circles) to 7±3 nEq/min² in antibody blocked animals (solid circles, P<0.0005). Taken together, the immune blocking experiments indicate that the anti-proUGn antibodies appear to bind proUGn, preventing their clearance by the kidney. The decrease in natriuresis in the immunoblocked animals provides further evidence that proUGn (or one of its renal metabolites) is the natriuretic peptide involved in the intero-renal axis.

Example 8

Determination of proUGn $ED_{50}$

Recombinant proUGn (r-proUGn) is bacterially synthesized in frame with (and fused to) the maltose binding protein (MBP), using the PMAL vector. A His tag and a TEV protease cleavage site are inserted between MBP and proUGn. The fusion protein is purified by binding to an amylose column, and proUGn is released by TEV cleavage of the immobilized material. Ni-sepharose beads are used to remove any free, uncleaved fusion protein and free MBP, as well as the recombinant TEV protease. The r-proUGn is then additionally purified by reverse-phase HPLC. Recovery of r-proUGn is monitored by Western blotting, and the absolute amount of propeptide recovered is established by quantitative amino acid analysis after acid hydrolysis.

After a 60-min control period, synthetic r-proUGn or purified native proUGn is infused iv over 60 min. Urine is collected at 30 min intervals up to 180 min after termination of proUGn infusion, and urine volume, sodium excretion, and potassium excretion are determined for each collection interval. Blood pressure is monitored continuously. Only one concentration of proUGn is administered to each animal due to the slow onset and long time course of the renal response to proUGn. The administered amount is calculated by assay of the stock solutions used to prepare the infused amounts, and titered to generate a dose-response relationship for Na excretion. The resulting plasma concentration is determined by assay of plasma sampled before and after the infusion.

Example 9

Determination of the Identity and Activity of Kidney proUGn Metabolites

HPLC analysis of urine collected after prolonged infusion of $^{35}$S-proUGn in Example 6, above, showed three possible kidney metabolites of proUGn (see FIG. 9b). The identity of each of the three possible metabolites is determined by mass spectral analysis of the corresponding HPLC fractions. Prior to mass spectral analysis, the peaks are subjected to an additional round of purification via anion or cation exchange chromatography and/or more sample is produced by scaling up the procedure described in Example 6. In a scale-up reaction, purified native proUGn is spiked with tracer amounts of radioactive pro-UGn and infused in several rats and the urine collected. The urine is then pooled and purified via a two-step reverse-phase/ion exchange purification protocol. The final fractions containing each of the possible proUGn metabolites are lyophilized and resuspended in a small volume of 50% methanol/0.1% formic acid. The masses of the peptides in these samples are determined using a mass spectrometer, for example a Bruker Reflex II MALDI-TOF instrument (Bruker Daltonics, Billerica, Mass., United States of America) or an Applied Biosystems Voyager™ 4700 MALDI-TOF/TOF instrument (Applied Biosystems, Foster City, Calif., United States of America) and those peptide fragments that are derived from proUGn are identified using the MASCOT search engine (Matrix Science, Boston, Mass., United States of America). In addition to this peptide mass fingerprinting approach, tandem MS can be performed to sequence individual peptides by MALDI-TOF/TOF. In cases in which the MALDI-TOF/TOF results are inconclusive (i.e., no significant matches are found between peptide sequences and the parental sequence), then tandem ESI-MS/MS data is obtained using either an ABI QSTAR (Applied Biosystems, Foster City, Calif., United States of America) or a Waters Micromass Q-TOF™ API-US (Waters, Milford, Mass., United States of America), both equipped with nano-ESI and nano-capillary LC systems, and the peptides derived from proUGn are identified from the tandem MS data using MASCOT.

Peptide sequences defined by MS analysis are synthesized according to established solid- or liquid-phase peptide synthesis techniques. Each synthetic peptide is infused into rats at a dose calculated on a mole-to-mole basis to be 100-fold above the ED$_{50}$ determined for proUGn.

In cases where activity is detected for any of the synthetic peptides at this high dose, a full dose/response relationship is determined. Additional experiments employ a radioactive version of the peptide, generated either by end-labeling the synthetic material or by collecting additional material from the renal metabolism of radioactive proUGn. This radioactive peptide is introduced into the renal artery of a naive animal, and urine is collected and analyzed by HPLC to determine whether the peptide resists intra-renal proteolysis.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference. Also expressly incorporated herein by reference are the contents of all citations of GenBank accession numbers, LocusID, and other computer database listings.

Barber J. D., et al., *Am. J. Physiol.*, 250, F895-F900 (1986).
Bettencourt P., et al., *Int. J. CardioL*, 93, 45-8 (2004).
Boffa J. J., et al., *J. Am. Soc. Nephrol.*, 15, 2358-65 (2004).
Burger A. J. and Silver M. A., *Lancet*, 20, 362, 998-9 (2003).
Carey R. M., *Circ. Res.*, 43, 19-23 (1978).
Carrithers S. L., et al., *Proc. Natl. Acad. Sci. U.S.A.*, 93, 14827-32 (1996).
Carrithers S. L., et al., *Braz. J. Med. Biol. Res.*, 32, 1337-44 (1999).
Carrithers S. L., et al., *Regul. Pept.*, 107, 87-95 (2002).
Carrithers S. L., et al., *Kidney Int.*, 65, 40-53 (2004).
Cianflone K., et al., *J. Lipid. Res.*, 30, 1727-33 (1989).
Cohen M. B., et al., *Biochem Biophys. Res. Commun.*, 209, 803-8 (1995).
Colindres R. E., et al., *Am. J. Physiol.*, 239, F265-F270 (1980).
Currie M. G., et al., *Proc. Natl. Acad. Sci. U.S.A.*, 89, 947-51 (1992).
Dharmsathaphorn K., et al., *Am. J. Physiol.*, 246, G204-G208 (1984).
English P. J., et al., *Obes. Res.*, 11, 839-44 (2003).
Fonteles M. C., et al., *Am. J. Physiol.*, 275, F191-F197 (1998).
Forte L. R., et al., *Am. J. Physiol. Renal Physiol.*, 278, F180-F191 (2000).
Forte L. R., *J. Clin. Invest.*, 112, 1138-41 (2003).
Fukae H., et al., *Nephron*, 84, 206-10 (2000).
Fukae H., et al., *Nephron*, 92, 373-8 (2002).
Giannella R. A. and Mann E. A., *Trans. Am. Clin. Climatol. Assoc.*, 114, 67-85 (2003).
Guarino A., et al., *Am. J. Physiol.*, 253, G775-G780 (1987).
Haberte D. A., et al., *Kidney Int. Suppl.*, 67, S242-S244 (1998).
Hamra F. K., et al., *Proc. Natl. Acad. Sci. U.S.A.*, 90, 10464-8 (1993).
Hamra F. K., et al., *Endocrinology*, 137, 257-65 (1996).
Huott P. A., et al., *J. Clin. Invest.*, 82, 514-23 (1988).
Inagami T., *J. Clin. Pharmacol.*, 34, 424-6 (1994).
Ise T., et al., *Kidney Int. Suppl.*, 67, S245-S249 (1998).
Kinoshita H., et al., *Nephron*, 81, 160-4 (1999).
Kinoshita H., et al., *Kidney Int.*, 52, 1028-34 (1997).
Kita T., et al., *Am. J. Physiol.*, 266, F342-F348 (1994).
Koller K. J., et al., *Science*, 252, 120-3 (1991).
Kuhn M., et al., *Circ. Res.*, 93, 700-9 (2003).
Lennane R. J., et al., *Clin. Sci. Mol. Med.*, 49, 433-6 (1975).
Lennane R. J., et al., *Clin. Sci. Mol. Med.*, 49, 437-40 (1975).
Li Z., et al., *Gastroenterology*, 109, 1863-75 (1995).
Li Z., et al., *Regul. Pept.*, 68, 45-56 (1997).
Lima A. A., et al., *Pharmacol. Toxicol.*, 70, 163-7 (1992).
Lorenz J. N. and Gruenstein E., *Am. J. Physiol.*, 276, F172-F177 (1999).
Lorenz J. N., et al., *J. Clin. Invest.*, 112, 1244-54 (2003).
Martin S., et al., *Endocrinology*, 140, 5022-9 (1999).
Matheson P. J., et al., *J. Surg. Res.*, 84, 57-63 (1999).
Mivazato M., et al., *FEBS Lett.*, 398, 170-4 (1996).
Moro F., et al., *Endocrinology*, 141, 2594-9 (2000).
Mu J., et al., *Pflugers Arch.*, 438, 159-64 (1999).
Nakazato M., et al., *Biochem. Biophys. Res. Commun.*, 220, 586-93 (1996).
Nilsson O., et al., *Cell Tissue Res.*, 248, 49-54 (1987).
Nishida Y., et al., *Am. J. Physiol.*, 274, R97-103 (1998).
Oda S., et al., *J. Pharmacol. Exp. Ther.*, 263, 241-5 (1992).

Ohyama Y., et al., *Biochem. Biophys. Res. Commun.*, 189, 336-42 (1992).
Perkins A., et al., *Gastroenterology*, 113, 1007-14 (1997).
Potthast R., et al., *Endocrinology*, 142, 3087-97 (2001).
Qian X., et al., *Endocrinology*, 141, 3210-24 (2000).
Sack R. B., *Annu. Rev. Microbiol.*, 29, 333-53 (1975).
Scheving L. A. and Jin W. H., *Am. J. Physiol.*, 277, C1177-C1183 (1999).
Schuck O., et al., *Int. J. Clin. Pharmacol. Ther. Toxicol.*, 19, 335-40 (1981).
Schulz S., et al., *Cell*, 63, 941-8 (1990).
Simpson F. O., *Lancet*, 2, 25-9 (1988).
Singer D. R., et al., *Am. J. Physiol.*, 274, F111-F119 (1998).
Skorecki K. L. and Brenner B. M., *Am. J. Med.*, 70, 77-88 (1981).
Solcia E., et al., Endocrine cells of the digestive system. In: Johnson L R (ed), Physiology of the gastrointestinal tract. New York: Raven Press, 111-30 (1987).
Stoupakis G., et al., *Heart Dis.*, 5, 215-23 (2003).
Swenson E. S., et al., *Biochem. Biophys. Res. Commun.*, 225, 1009-14 (1996).
Thomas C. J. and Woods R. L., *Hypertension*, 41, 279-85 (2003).
Tsukahara H., et al., *Pediatr. Int.*, 43, 267-9 (2001).
Vaandrager A. B., *Mol. Cell. Biochem.*, 230, 73-83 (2002).
Villarreal D., et al., *Am. J. Physiol.*, 258, R232-R239 (1990).
Vilsboll T., et al., *Regul. Pept.*, 114, 115-21 (2003).
von Geldern T. W., et al., *Mol. Pharmacol.*, 38, 771-8 (1990).
Antibodies: a Laboratory Manual. In: Harlow ELD (ed), New York, Cold Spring Harbor Laboratory Publications (2004).

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for treating a disorder characterized by salt retention, fluid retention, and combinations thereof, in a patient in need thereof, the method comprising administering an effective amount of preprouroguanylin, prouroguanylin, or analog thereof, to the patient, thereby producing diuresis, natriuresis, or a combination thereof, wherein said analog comprises preprouroguanylin or prouroguanylin modified by the addition of a non-peptide moiety selected from the group consisting of a radiolabelling component, a fluorescent moiety, a fatty acid group, a carbohydrate, and a polymer.

2. The method of claim 1, wherein the disorder is selected from the group consisting of kidney disease, heart disease, liver disease, hypertension, and combinations thereof.

3. The method of claim 1, wherein the preprouroguanylin, prouroguanylin, or analog thereof, is administered by infusion.

4. The method of claim 1, wherein the preprouroguanylin, prouroguanylin, or analog thereof, is selected from the group consisting of a synthetic, natural, and recombinant preprouroguanylin, prouroguanylin, or analog thereof.

5. The method of claim 1, wherein the effective amount of preprouroguanylin, prouroguanylin, or analog thereof, is administered in combination with at least one other drug that has diuretic properties, natriuretic properties, or both diuretic and natriuretic properties.

6. The method of claim 5, wherein the other drug is a diuretic.

7. The method of claim 6, wherein the diuretic is selected from the group consisting of carbonic anhydrase inhibitors, thiazide-like diuretics, loop or high ceiling diuretics, and potassium-sparing diuretics.

8. The method of claim 6, wherein the diuretic is selected from the group consisting of furosemide, bumetadine, torsemide, hydrochlorothiazide, triamterine, indapamide, ethocrinic acid, spironolactone, and metolazone.

* * * * *

SEQUENCE LISTING

```
<160> NUMBER OF SEQ ID NOS: 12

<210> SEQ ID NO 1
<211> LENGTH: 18
<212> TYPE: PRT
<213> ORGANISM: Rattus norvegicus

<400> SEQUENCE: 1

Thr Ile Ala Thr Asp Glu Cys Glu Leu Cys Ile Asn Val Ala Cys Thr
1               5                   10                  15

Gly Cys

<210> SEQ ID NO 2
<211> LENGTH: 16
<212> TYPE: PRT
<213> ORGANISM: Homo sapiens

<400> SEQUENCE: 2

Asn Asp Asp Cys Glu Leu Cys Val Asn Val Ala Cys Thr Gly Cys Leu
1               5                   10                  15

<210> SEQ ID NO 3
<211> LENGTH: 106
<212> TYPE: PRT
<213> ORGANISM: Rattus norvegicus

<400> SEQUENCE: 3

Met Ser Gly Ser Gln Leu Trp Ala Ala Val Leu Leu Leu Leu Val Leu
1               5                   10                  15

Gln Ser Ala Gln Gly Val Tyr Ile Lys Tyr His Gly Phe Gln Val Gln
            20                  25                  30

Leu Glu Ser Val Lys Lys Leu Asn Glu Leu Glu Glu Lys Gln Met Ser
        35                  40                  45

Asp Pro Gln Gln Gln Lys Ser Gly Leu Leu Pro Asp Val Cys Tyr Asn
    50                  55                  60

Pro Ala Leu Pro Leu Asp Leu Gln Pro Val Cys Ala Ser Gln Glu Ala
65                  70                  75                  80

Ala Ser Thr Phe Lys Ala Leu Arg Thr Ile Ala Thr Asp Glu Cys Glu
                85                  90                  95

Leu Cys Ile Asn Val Ala Cys Thr Gly Cys
            100                 105
```

```
<210> SEQ ID NO 4
<211> LENGTH: 112
<212> TYPE: PRT
<213> ORGANISM: Homo sapiens

<400> SEQUENCE: 4

Met Gly Cys Arg Ala Ala Ser Gly Leu Leu Pro Val Ala Val Val
1               5                   10                  15

Leu Leu Leu Leu Leu Gln Ser Thr Gln Ser Val Tyr Ile Gln Tyr Gln
                20                  25                  30

Gly Phe Arg Val Gln Leu Glu Ser Met Lys Lys Leu Ser Asp Leu Glu
                35                  40                  45

Ala Gln Trp Ala Pro Ser Pro Arg Leu Gln Ala Gln Ser Leu Leu Pro
        50                  55                  60

Ala Val Cys His His Pro Ala Leu Pro Gln Asp Leu Gln Pro Val Cys
65                  70                  75                  80

Ala Ser Gln Glu Ala Ser Ser Ile Phe Lys Thr Leu Arg Thr Ile Ala
                85                  90                  95

Asn Asp Asp Cys Glu Leu Cys Val Asn Val Ala Cys Thr Gly Cys Leu
                100                 105                 110

<210> SEQ ID NO 5
<211> LENGTH: 86
<212> TYPE: PRT
<213> ORGANISM: Homo sapiens

<400> SEQUENCE: 5

Val Tyr Ile Gln Tyr Gln Gly Phe Arg Val Gln Leu Glu Ser Met Lys
1               5                   10                  15

Lys Leu Ser Asp Leu Glu Ala Gln Trp Ala Pro Ser Pro Arg Leu Gln
                20                  25                  30

Ala Gln Ser Leu Leu Pro Ala Val Cys His His Pro Ala Leu Pro Gln
                35                  40                  45

Asp Leu Gln Pro Val Cys Ala Ser Gln Glu Ala Ser Ser Ile Phe Lys
        50                  55                  60

Thr Leu Arg Thr Ile Ala Asn Asp Asp Cys Glu Leu Cys Val Asn Val
65                  70                  75                  80

Ala Cys Thr Gly Cys Leu
                85

<210> SEQ ID NO 6
<211> LENGTH: 15
<212> TYPE: PRT
<213> ORGANISM: Rattus norvegicus

<400> SEQUENCE: 6

Pro Asn Thr Cys Glu Ile Cys Ala Tyr Ala Ala Cys Thr Gly Cys
1               5                   10                  15

<210> SEQ ID NO 7
<211> LENGTH: 15
<212> TYPE: PRT
<213> ORGANISM: Rattus norvegicus

<400> SEQUENCE: 7

Pro Ala Leu Pro Leu Asp Leu Gln Pro Val Cys Ala Ser Gln Glu
1               5                   10                  15

<210> SEQ ID NO 8
<211> LENGTH: 85
```

```
<212> TYPE: PRT
<213> ORGANISM: Rattus norvegicus

<400> SEQUENCE: 8

Val Tyr Ile Lys Tyr His Gly Phe Gln Val Gln Leu Glu Ser Val Lys
1               5                   10                  15

Lys Leu Asn Glu Leu Glu Glu Lys Gln Met Ser Asp Pro Gln Gln Gln
            20                  25                  30

Lys Ser Gly Leu Leu Pro Asp Val Cys Tyr Asn Pro Ala Leu Pro Leu
        35                  40                  45

Asp Leu Gln Pro Val Cys Ala Ser Gln Glu Ala Ala Ser Thr Phe Lys
    50                  55                  60

Ala Leu Arg Thr Ile Ala Thr Asp Glu Cys Glu Leu Cys Ile Asn Val
65                  70                  75                  80

Ala Cys Thr Gly Cys
                85

<210> SEQ ID NO 9
<211> LENGTH: 115
<212> TYPE: PRT
<213> ORGANISM: Rattus norvegicus

<400> SEQUENCE: 9

Met Asn Ala Trp Leu Leu Ser Val Leu Cys Leu Leu Gly Ala Leu Ala
1               5                   10                  15

Val Leu Val Glu Gly Val Thr Val Gln Asp Gly Asp Leu Ser Phe Pro
            20                  25                  30

Leu Glu Ser Val Lys Gln Leu Lys His Leu Arg Glu Val Gln Glu Pro
        35                  40                  45

Thr Leu Met Ser His Lys Lys Phe Ala Leu Arg Leu Pro Lys Pro Val
    50                  55                  60

Ala Pro Glu Leu Cys Ser Gln Ser Ala Phe Pro Glu Ala Leu Arg Pro
65                  70                  75                  80

Leu Cys Glu Lys Pro Asn Ala Glu Glu Ile Leu Gln Arg Leu Glu Ala
                85                  90                  95

Ile Ala Gln Asp Pro Asn Thr Cys Glu Ile Cys Ala Tyr Ala Ala Cys
                100                 105                 110

Thr Gly Cys
        115

<210> SEQ ID NO 10
<211> LENGTH: 14
<212> TYPE: PRT
<213> ORGANISM: Rattus norvegicus

<400> SEQUENCE: 10

Gln Gln Gln Lys Ser Gly Leu Leu Pro Asp Val Cys Tyr Asn
1               5                   10

<210> SEQ ID NO 11
<211> LENGTH: 14
<212> TYPE: PRT
<213> ORGANISM: Rattus norvegicus

<400> SEQUENCE: 11

Val Gln Asp Gly Asp Leu Ser Phe Pro Leu Glu Ser Val Lys
1               5                   10

<210> SEQ ID NO 12
<211> LENGTH: 15
```

```
<212> TYPE: PRT
<213> ORGANISM: Rattus norvegicus

<400> SEQUENCE: 12

Leu Cys Glu Lys Pro Asn Ala Glu Glu Ile Leu Gln Arg Leu Glu
1               5                   10                  15
```